US007488826B2

(12) United States Patent
Zhang et al.

(10) Patent No.: US 7,488,826 B2
(45) Date of Patent: Feb. 10, 2009

(54) SUBSTITUTED PYRROLINE KINASE INHIBITORS

(75) Inventors: Han-Cheng Zhang, Landsale, PA (US); Bruce E. Maryanoff, Forest Grove, PA (US); Hong Ye, Lansdale, PA (US)

(73) Assignee: Janssen Pharmaceutica N.V. (BE)

( * ) Notice: Subject to any disclaimer, the term of this patent is extended or adjusted under 35 U.S.C. 154(b) by 430 days.

(21) Appl. No.: 10/792,522

(22) Filed: Mar. 3, 2004

(65) Prior Publication Data

US 2004/0192718 A1 Sep. 30, 2004

Related U.S. Application Data

(60) Provisional application No. 60/458,127, filed on Mar. 27, 2003.

(51) Int. Cl.
*C07D 471/04* (2006.01)
(52) U.S. Cl. ..................................................... 546/113
(58) Field of Classification Search ................. 546/112, 546/113
See application file for complete search history.

(56) References Cited

U.S. PATENT DOCUMENTS

| 5,057,614 | A | 10/1991 | Davis et al. |
| 6,849,643 | B2 | 2/2005 | Zhang et al. |
| 6,987,110 | B2 | 1/2006 | Zhang et al. |
| 7,001,906 | B2 * | 2/2006 | Prudhomme et al. ........ 514/250 |
| 7,125,878 | B2 | 10/2006 | Zhang et al. |
| 2004/0054180 | A1 | 3/2004 | Zhang et al. |
| 2004/0259928 | A1 | 12/2004 | Zhang et al. |
| 2005/0004201 | A1 | 1/2005 | Zhang et al. |
| 2005/0004202 | A1 | 1/2005 | Zhang et al. |
| 2006/0205762 | A1 | 9/2006 | Zhang et al. |
| 2006/0205763 | A1 | 9/2006 | Zhang et al. |

FOREIGN PATENT DOCUMENTS

| WO | WO 95/07910 A1 | 3/1995 |
| WO | WO 00/21927 A2 | 4/2000 |
| WO | WO 00/38675 | 7/2000 |
| WO | WO 03/002563 | 1/2003 |
| WO | WO 03/095452 | 11/2003 |

OTHER PUBLICATIONS

PCT International Search Report, dated Jul. 16, 2004, for PCT Int'l. Appln. No. PCT/US2004/006424.
Database Beilstein, Beilstein Institute for Organic Chemistry, Frankfurt-Main, De, Database Accession No. 5386104(BRN) and J. Med. Chem., vol. 35, No. 6, 1992, pp. 994-1001.
Database Beilstein, Beilstein Institute for Organic Chemistry, Frankfurt-Main, De, Database Accession No. 5366323 (BRN) and Biochem. Pharmacol., vol. 50, No. 2, 1995, pp. 197-204.
Davis P.D. et al., "Inhibitors of Protein Kinase C 1. 2,3-Bisarylmaleimides", Journal of Medicinal Chemistry, American Chemical Society, Washington, US, vol. 35, No. 1, 1992, pp. 177-184.
Hers, I. et al., "The protein kinase C inhibitors bisindolylmaleimide I (GF 109203x) and IX (Ro 31-8220) are potent inhibitors of glycogen synthase kinaase-3 activity", FEBS Letters, Elsevier Science Publishers, Amsterdam, NL., vol. 460, No. 3, Nov. 5, 1999, pp. 433-436.
Smith, D.G. et al., "3-Anilino-4-arylmaleimides: potent and selective inhibitors of glycogen synthase Kinase=3 (GSK-3)", Bioorganic & Medicinal Chemistry Letters, Oxford, GB, vol. 11, No. 5, Mar. 12, 2001, pp. 635-639.

* cited by examiner

*Primary Examiner*—Patricia L Morris

(57) ABSTRACT

The present invention is directed to novel substituted pyrroline compounds useful as kinase or dual-kinase inhibitors and methods for treating or ameliorating a kinase or dual-kinase mediated disorder.

31 Claims, No Drawings

SUBSTITUTED PYRROLINE KINASE INHIBITORS

This application claims benefit of provisional patent application Ser. No. 60/458,127 filed Mar. 27, 2003 hereby incorporated by reference herein.

FIELD OF THE INVENTION

This invention is directed to certain novel compounds, methods for producing them and methods for treating or ameliorating a kinase or dual-kinase mediated disorder. More particularly, this invention is directed to substituted pyrroline compounds useful as selective kinase or dual-kinase inhibitors, methods for producing such compounds and methods for treating or ameliorating a kinase or dual-kinase mediated disorder.

BACKGROUND OF THE INVENTION

Patent application WO 00/38675 discloses disubstituted maleimide compounds of Formula compounds as GSK-3 (glycogen synthase kinase-3) inhibitors of Formula (A), (B) and (C):

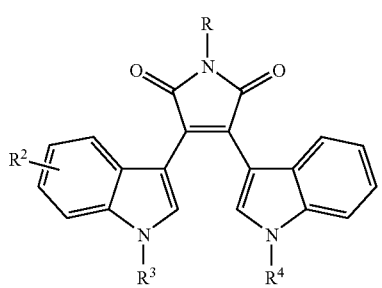

(A)

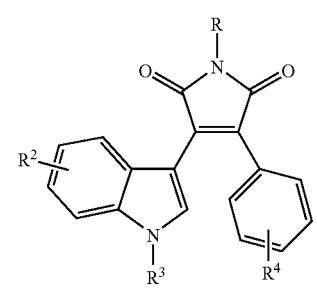

(B)

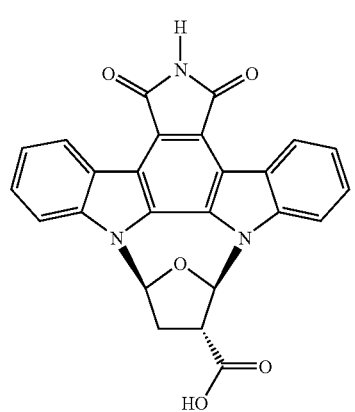

(C)

wherein, for Formula (A), R is hydrogen; $R^2$ is hydrogen, 5-O-n-Pr, 5-Ph, 5-$CO_2$Me or 5-$NO_2$; $R^3$ is Me or $(CH_2)_3OH$, and; $R^4$ is Me, n-Pr, —$(CH_2)_3$X, wherein X is selected from CN, $NH_2$, $CO_2H$, $CONH_2$ or OH; and, wherein, for Formula (B), R is hydrogen; $R^2$ is hydrogen; $R^3$ is Me or a group —$(CH_2)_3$Y, wherein Y is $NH_2$ or OH; and, $R^4$ is 2-Cl or 2,4-di-Cl.

Patent application WO 00/21927 describes 3-amino-4-arymaleimide compounds of Formula (I):

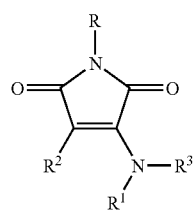

(I)

or a pharmaceutically acceptable derivative thereof, wherein: R is hydrogen, alkyl, aryl or aralkyl; $R^1$ is hydrogen, alkyl, aralkyl, hydroxyalkyl or alkoxyalkyl; $R^2$ is substituted or unsubstituted aryl or substituted or unsubstituted heterocyclyl; $R^3$ is hydrogen, substituted or unsubstituted alkyl, cycloalkyl, alkoxyalkyl, substituted or unsubstituted aryl, substituted or unsubstituted heterocyclyl or aralkyl wherein the aryl moiety is substituted or unsubstituted; or, $R^1$ and $R^3$ together with the nitrogen to which they are attached form a single or fused, optionally substituted, saturated or unsaturated heterocyclic ring and a method for the treatment of conditions associated with a need for inhibition of GSK-3, such as diabetes, dementias such as Alzheimer's disease and manic depression.

U.S. Pat. No. 5,057,614 to Davis, et. al., describes substituted pyrrole compounds of formula (I):

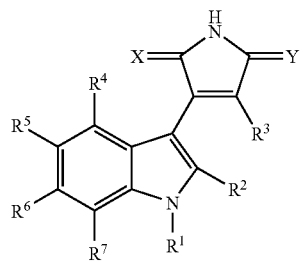

(I)

wherein $R^1$ signifies hydrogen, alkyl, aryl (limited to phenyl), aralkyl (limited to phenylalkyl), alkoxyalkyl, hydroxyalkyl, haloalkyl, aminoalkyl, monoalkylaminoalkyl, dialkylaminoalkyl, trialkylaminoalkyl, aminoalkylaminoalkyl, azidoalkyl, acylaminoalkyl, acylthioalkyl, alkylsulphonylaminoalkyl, arylsulphonylaminoalkyl, mercaptoalkyl, alkylthioalkyl, alkylsulphinylalkyl, alkylsulphonylalkyl, alkylsulphonyloxyalkyl, alkylcarbonyloxyalkyl, cyanoalkyl, amidinoalkyl, isothiocyanatoalkyl, glucopyranosyl, carboxyalkyl, alkoxycarbonylalkyl, aminocarbonylalkyl, hydroxyalkylthioalkyl, mercaptoalkylthioalkyl, arylthioalkyl or carboxyalkylthioalkyl or a group of the formula —$(CH_2)_n$—W-Het (a), —$(CH_2)_n$-T-C(=V)-Z (b), —(CH₂)ₙ—NH—C(=O)-Im (c), or —(CH₂)ₙ—NH—C(=NH)—Ar (d)

in which Het signifies a heterocyclyl group, W signifies NH, S or a bond, T signifies NH or S, V signifies O, S, NH, NNO₂, NCN or CHNO₂, Z signifies alkylthio, amino, monoalkylamino or dialkylamino, Im signifies 1-imidazolyl, Ar signifies aryl, and n stands for 2-6; $R^2$ signifies hydrogen, alkyl, aralkyl, alkoxyalkyl, hydroxyalkyl, haloalkyl, aminoalkyl, monoalkylaminoalkyl, dialkylaminoalkyl, acylaminoalkyl, alkylsulphonylaminoalkyl, arylsulphonylaminoalkyl, mercaptoalkyl, alkylthioalkyl, carboxyalkyl, alkoxycarbonylalkyl, aminocarbonylalkyl, alkylthio or alkylsulphinyl; $R^3$ signifies a carbocyclic or heterocyclic aromatic group; $R^4$, $R^5$, $R^6$ and $R^7$ each independently signify hydrogen, halogen, hydroxy, alkoxy, aryloxy, haloalkyl, nitro, amino, acylamino, monoalkylamino, dialkylamino, alkylthio, alkylsulphinyl or alkylsulphonyl; and one of X and Y signifies O and the other signifies O, S, (H,OH) or (H,H); with the proviso that $R^1$ has a significance different from hydrogen when $R^2$ signifies hydrogen, $R^3$ signifies 3-indolyl or 6-hydroxy-3-indolyl, $R^4$, $R^5$ and $R^7$ each signify hydrogen, $R^6$ signifies hydrogen or hydroxy and X and Y both signify O and when $R^2$ signifies hydrogen, $R^3$ signifies 3-indolyl, $R^4$, $R^5$, $R^6$ and $R^7$ each signify hydrogen, X signifies (H,H) and Y signifies O; as well as pharmaceutically acceptable salts of acidic compounds of formula I with bases and of basic compounds of formula I with acids, as protein kinase C inhibitors and as therapeutically active substances for the use in control or prevention of inflammatory, immunological, bronchopulmonary and cardiovascular disorders.

An associated published paper (Davis, et. al., *J. Med. Chem.* 1992, 35, 177-184), disclosed a compound of formula (I) wherein $R^4$, $R^5$, $R^6$ and $R^7$ signify hydrogen; $R^1$ signifies methyl; X and Y signify O; and $R^3$ signifies 3-(7-aza-1-methylindolyl) as a protein kinase C inhibitor ($IC_{50}$=2.9 µM).

Patent application WO 95/07910 describes heterocyclylindole derivatives of formula (I):

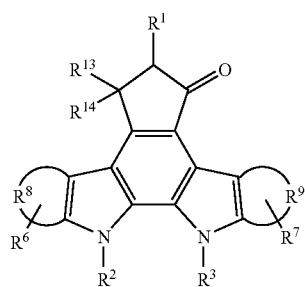

as antiviral agents. Preparation of compounds of formula (I) include use of indolyl(7-azaindolyl)maleimide compounds and bis(7-azaindolyl)maleimide compounds as reaction intermediates.

The substituted pyrroline compounds of the present invention have not been heretofore disclosed.

Accordingly, it is an object of the present invention to provide substituted pyrroline compounds useful as a kinase or dual-kinase inhibitor (in particular, a kinase selected from protein kinase C or glycogen synthase kinase-3; and, more particularly, a kinase selected from protein kinase C α, protein kinase C β-II, protein kinase C γ or glycogen synthase kinase-3β), methods for their production and methods for treating or ameliorating a kinase or dual-kinase mediated disorder.

SUMMARY OF THE INVENTION

The present invention is directed to substituted pyrroline compounds of Formula (I):

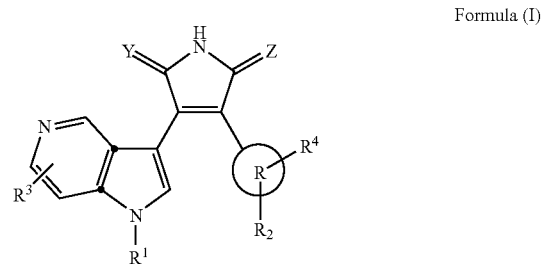

Formula (I)

wherein

R is selected from the group consisting of $R_a$, —$C_{1-8}$alkyl-$R_a$, —$C_{2-8}$alkenyl-$R_a$, —$C_{2-8}$alkynyl-$R_a$ and cyano;

$R_a$ is selected from the group consisting of cycloalkyl, heterocyclyl, aryl and heteroaryl;

$R^1$ is selected from the group consisting of hydrogen, —$C_{1-8}$alkyl-$R^5$, —$C_{2-8}$alkenyl-$R^5$, —$C_{2-8}$alkynyl-$R^5$, —C(O)—($C_{1-8}$)alkyl-$R^9$, —C(O)-aryl-$R^8$, —C(O)—O—($C_{1-8}$)alkyl-$R^9$, —C(O)—O-aryl-$R^8$, —C(O)—NH($C_{1-8}$ alkyl-$R^9$), —C(O)—NH(aryl-$R^8$), —C(O)—N($C_{1-8}$ alkyl-$R^9$)₂, —SO₂—($C_{1-8}$)alkyl-$R^9$, —SO₂-aryl-$R^8$, -cycloalkyl-$R^6$, -heterocyclyl-$R^6$, -aryl-$R^6$ and -heteroaryl-$R^6$; wherein heterocyclyl and heteroaryl are attached to the azaindole nitrogen atom in the one position via a heterocyclyl or heteroaryl ring carbon atom;

$R^5$ is 1 to 2 substituents independently selected from the group consisting of hydrogen, —O—($C_{1-8}$)alkyl, —O—($C_{1-8}$)alkyl-OH, —O—($C_{1-8}$)alkyl-O—($C_{1-8}$)alkyl, —O—($C_{1-8}$)alkyl-NH₂, —O—($C_{1-8}$)alkyl-NH($C_{1-8}$ alkyl), —O—($C_{1-8}$)alkyl-N($C_{18}$alkyl)₂, —O—($C_{1-8}$)alkyl-S—($C_{1-8}$)alkyl, —O—($C_{1-8}$)alkyl-SO₂—($C_{1-8}$)alkyl, —O—($C_{1-8}$)alkyl-SO₂—NH₂, —O—($C_{1-8}$)alkyl-SO₂—NH($C_{1-8}$alkyl), —O—($C_{1-8}$)alkyl-SO₂—N($C_{1-8}$alkyl)₂, —O—C(O)H, —O—C(O)—($C_{1-8}$)alkyl, —O—C(O)—NH₂, —O—C(O)—NH($C_{1-8}$alkyl), —O—C(O)—N($C_{1-8}$alkyl)₂, —O—($C_{1-8}$)alkyl-C(O)H, —O—($C_{1-8}$)alkyl-C(O)—($C_{1-8}$)alkyl, —O—($C_{1-8}$)alkyl-CO₂H, —O—($C_{1-8}$)alkyl-C(O)—O—($C_{1-8}$)alkyl, —O—($C_{1-8}$)alkyl-C(O)—NH₂, —O—($C_{1-8}$)alkyl-C(O)—NH($C_{1-8}$ alkyl), —O—($C_{1-8}$)alkyl-C(O)—N($C_{1-8}$alkyl)₂, —C(O)H, —C(O)—($C_{1-8}$)alkyl, —CO₂H, —C(O)—O—($C_{1-8}$)alkyl, —C(O)—NH₂, —C(NH)—NH₂, —C(O)—NH($C_{1-8}$ alkyl), —C(O)—N($C_{1-8}$alkyl)₂, —SH, —S—($C_{1-8}$) alkyl, —S—($C_{1-8}$)alkyl-S—($C_{1-8}$)alkyl, —S—($C_{1-8}$) alkyl-O—($C_{1-8}$)alkyl, —S—($C_{1-8}$)alkyl-O—($C_{1-8}$)alkyl-OH, —S—($C_{1-8}$)alkyl-O—($C_{1-8}$)alkyl-NH₂, —S—($C_{1-8}$)alkyl-O—($C_{1-8}$)alkyl-NH($C_{1-8}$alkyl), —S—($C_{1-8}$)alkyl-O—($C_{1-8}$)alkyl-N($C_{1-8}$alkyl)₂, —S—($C_{1-8}$) alkyl-NH($C_{1-8}$ alkyl), —SO₂—($C_{1-8}$)alkyl, —SO₂—NH₂, —SO₂—NH($C_{1-8}$alkyl), —SO₂—N($C_{1-8}$alkyl)₂, —N—$R^7$, cyano, (halo)₁₋₃, hydroxy, nitro, oxo, -cycloalkyl-$R^6$, -heterocyclyl-$R^6$, -aryl-$R^6$ and -heteroaryl-$R^6$;

$R^6$ is 1 to 4 substituents attached to a carbon or nitrogen atom independently selected from the group consisting of hydrogen, —$C_{1-8}$alkyl, —$C_{2-8}$alkenyl, —$C_{2-8}$alkynyl, —C(O)

H, —C(O)—(C$_{1-8}$)alkyl, —CO$_2$H, —C(O)—O—(C$_{1-8}$) alkyl, —C(O)—NH$_2$, —C(NH)—NH$_2$, —C(O)—NH (C$_{1-8}$ alkyl), —C(O)—N(C$_{1-8}$alkyl)$_2$, —SO$_2$—(C$_{1-8}$) alkyl, —SO$_2$—NH$_2$, —SO$_2$—NH(C$_{1-8}$alkyl), —SO$_2$—N (C$_{1-8}$alkyl)$_2$, —(C$_{1-8}$)alkyl-N—R$^7$, —(C$_{1-8}$)alkyl-(halo)$_{1-3}$, —(C$_{1-8}$)alkyl-OH, -aryl-R$^8$, —(C$_{1-8}$)alkyl-aryl-R$^8$ and —(C$_{1-8}$)alkyl-heteroaryl-R$^8$;

with the proviso that, when R$^6$ is attached to a carbon atom, R$^6$ is further selected from the group consisting of —C$_{1-8}$ alkoxy, —(C$_{1-8}$)alkoxy-(halo)$_{1-3}$, —SH, —S—(C$_{1-8}$) alkyl, —N—R$^7$, cyano, halo, hydroxy, nitro, oxo and -heteroaryl-R$^8$;

R$^7$ is 2 substituents independently selected from the group consisting of hydrogen, —C$_{1-8}$alkyl, —C$_{2-8}$alkenyl, —C$_{2-8}$ alkynyl, —(C$_{1-8}$)alkyl-OH, —(C$_{1-8}$)alkyl-O—(C$_{1-8}$) alkyl, —(C$_{1-8}$)alkyl-NH$_2$, —(C$_{1-8}$)alkyl-NH(C$_{1-8}$ alkyl), —(C$_{1-8}$)alkyl-N(C$_{1-8}$alkyl)$_2$, —(C$_{1-8}$)alkyl-S—(C$_{1-8}$)alkyl, —C(O)H, —C(O)—(C$_{1-8}$)alkyl, —C(O)—O—(C$_{1-8}$) alkyl, —C(O)—NH$_2$, —C(O)—NH(C$_{1-8}$alkyl), —C(O)—N(C$_{1-8}$alkyl)$_2$, —SO$_2$—(C$_{1-8}$)alkyl, —SO$_2$—NH$_2$, —SO$_2$—NH(C$_{1-8}$alkyl), —SO$_2$—N(C$_{1-8}$alkyl)$_2$, —C(N)—NH$_2$, -cycloalkyl-R$^8$, —(C$_{1-8}$)alkyl-heterocyclyl-R$^8$, -aryl-R$^8$, —(C$_{1-8}$)alkyl-aryl-R$^8$ and —(C$_{1-8}$)alkyl-heteroaryl-R$^8$;

R$^8$ is 1 to 4 substituents attached to a carbon or nitrogen atom independently selected from the group consisting of hydrogen, —C$_{1-8}$alkyl, —(C$_{1-8}$)alkyl-(halo)$_{1-3}$ and —(C$_{1-8}$) alkyl-OH;

with the proviso that, when R$^8$ is attached to a carbon atom, R$^8$ is further selected from the group consisting of —C$_{1-8}$ alkoxy, —NH$_2$, —NH(C$_{1-8}$alkyl), —N(C$_{1-8}$alkyl)$_2$, cyano, halo, —(C$_{1-8}$)alkoxy-(halo)$_{1-3}$, hydroxy and nitro;

R$^9$ is 1 to 2 substituents independently selected from the group consisting of hydrogen, —C$_{1-8}$alkoxy, —NH$_2$, —NH(C$_{1-8}$alkyl), —N(C$_{1-8}$alkyl)$_2$, cyano, (halo)$_{1-3}$, hydroxy and nitro;

R$^2$ is one substituent attached to a carbon or nitrogen atom selected from the group consisting of hydrogen, —C$_{1-8}$alkyl-R$^5$, —C$_{2-8}$alkenyl-R$^5$, —C$_{2-8}$alkynyl-R$^5$, —C(O)H, —C(O)—(C$_{1-8}$)alkyl-R$^9$, —C(O)—NH$_2$, —C(O)—NH(C$_{1-8}$alkyl-R$^9$), —C(O)—N(C$_{1-8}$alkyl-R$^9$)$_2$, —C(O)—NH (aryl-R$^8$), —C(O)-cycloalkyl-R$^8$, —C(O)-heterocyclyl-R$^8$, —C(O)-aryl-R$^8$, —C(O)-heteroaryl-R$^8$, —CO$_2$H, —C(O)—O—(C$_{1-8}$)alkyl-R$^9$, —C(O)—O-aryl-R$^8$, —SO$_2$—(C$_{1-8}$)alkyl-R$^9$, —SO$_2$-aryl-R$^8$, -cycloalkyl-R$^6$, -aryl-R$^6$ and —(C$_{1-8}$)alkyl-N—R$^7$;

with the proviso that, when R$^2$ is attached to a carbon atom, R$^2$ is further selected from the group consisting of —C$_{1-8}$ alkoxy-R$^5$, —N—R$^7$, cyano, halogen, hydroxy, nitro, oxo, -heterocyclyl-R$^6$ and -heteroaryl-R$^6$;

R$^3$ is 1 to 3 substituents attached to a carbon atom independently selected from the group consisting of hydrogen, —C$_{1-8}$alkyl-R$^{10}$, —C$_{2-8}$alkenyl-R$^{10}$, —C$_{2-8}$alkynyl-R$^{10}$, —C$_{1-8}$alkoxy-R$^{10}$, —C(O)H, —C(O)—(C$_{1-8}$)alkyl-R$^9$, —C(O)—NH$_2$, —C(O)—NH(C$_{1-8}$alkyl-R$^9$), —C(O)—N(C$_{1-8}$alkyl-R$^9$)$_2$, —C(O)-cycloalkyl-R$^8$, —C(O)-heterocyclyl-R$^8$, —C(O)-aryl-R$^8$, —C(O)-heteroaryl-R$^8$, —C(NH)—NH$_2$, —CO$_2$H, —C(O)—O—(C$_{1-8}$)alkyl-R$^9$, —C(O)—O-aryl-R$^8$, —SO$_2$—(C$_{1-8}$)alkyl-R$^9$, —SO$_2$-aryl-R$^8$, —N—R$^7$, cyano, halogen, hydroxy, nitro, -cycloalkyl-R$^8$, -heterocyclyl-R$^8$, -aryl-R$^8$ and -heteroaryl-R$^8$;

R$^4$ is 1 to 4 substituents attached to a carbon atom independently selected from the group consisting of hydrogen, —C$_{1-8}$alkyl-R$^{10}$, —C$_{2-8}$alkenyl-R$^{10}$, —C$_{2-8}$alkynyl-R$^{10}$, —C$_{1-8}$alkoxy-R$^{10}$, —C(O)H, —C(O)—(C$_{1-8}$)alkyl-R$^9$, —C(O)—NH$_2$, —C(O)—NH(C$_{1-8}$alkyl-R$^9$), —C(O)—N (C$_{1-8}$alkyl-R$^9$)$_2$, —C(O)-cycloalkyl-R$^8$, —C(O)-heterocyclyl-R$^8$, —C(O)-aryl-R$^8$, —C(O)-heteroaryl-R$^8$, —C(NH)—NH$_2$, —CO$_2$H, —C(O)—O—(C$_{1-8}$)alkyl-R$^9$, —C(O)—O-aryl-R$^8$, —SH, —S—(C$_{1-8}$)alkyl-R$^{10}$, —SO$_2$—(C$_{1-8}$)alkyl-R$^9$, —SO$_2$-aryl-R$^8$, —SO$_2$—NH$_2$, —SO$_2$—NH(C$_{1-8}$alkyl-R$^9$), —SO$_2$—N(C$_{1-8}$alkyl-R$^9$)$_2$, —N—R$^7$, cyano, halogen, hydroxy, nitro, -cycloalkyl-R$^8$, -heterocyclyl-R$^8$, -aryl-R$^8$ and -heteroaryl-R$^8$;

R$^{10}$ is 1 to 2 substituents independently selected from the group consisting of hydrogen, —NH$_2$, —NH(C$_{1-8}$alkyl), —N(C$_{1-8}$alkyl)$_2$, cyano, (halo)$_{1-3}$, hydroxy, nitro and oxo; and, Y and Z are independently selected from the group consisting of O, S, (H,OH) and (H,H); with the proviso that one of Y and Z is O and the other is selected from the group consisting of O, S, (H,OH) and (H,H);

and pharmaceutically acceptable salts thereof.

The present invention is directed to substituted pyrroline compounds useful as a selective kinase or dual-kinase inhibitor; in particular, a kinase selected from protein kinase C or glycogen synthase kinase-3; and, more particularly, a kinase selected from protein kinase C α, protein kinase C β-II, protein kinase C γ or glycogen synthase kinase-3β.

The present invention is also directed to methods for producing the instant substituted pyrroline compounds and pharmaceutical compositions and medicaments thereof.

The present invention is further directed to methods for treating or ameliorating a kinase or dual-kinase mediated disorder. In particular, the method of the present invention is directed to treating or ameliorating a kinase or dual-kinase mediated disorder such as, but not limited to, cardiovascular diseases, diabetes, diabetes-associated disorders, inflammatory diseases, immunological disorders, dermatological disorders, oncological disorders and CNS disorders.

DETAILED DESCRIPTION OF THE INVENTION

Embodiments of the present invention include compounds of Formula (I) wherein, preferably, R is selected from the group consisting of R$_a$, —C$_{1-4}$alkyl-R$_a$, —C$_{2-4}$alkenyl-R$_a$, —C$_{2-4}$alkynyl-R$_a$ and cyano.

Embodiments of the present invention include compounds of Formula (I) wherein, preferably, R$_a$ is selected from the group consisting of heterocyclyl, aryl and heteroaryl.

More preferably, R$_a$ is selected from the group consisting of dihydro-pyranyl, phenyl, naphthyl, thienyl, pyrrolyl, imidazolyl, pyrazolyl, pyridinyl, azaindolyl, indazolyl, benzofuryl, benzothienyl, dibenzofuryl and dibenzothienyl.

Embodiments of the present invention include compounds of Formula (I) wherein, preferably, R$^1$ is selected from the group consisting of hydrogen, —C$_{1-4}$alkyl-R$^5$, —C$_{2-4}$alkenyl-R$^5$, —C$_{2-4}$alkynyl-R$^5$, —C(O)—(C$_{1-4}$)alkyl-R$^9$, —C(O)-aryl-R$^8$, —C(O)—O—(C$_{1-4}$)alkyl-R$^9$, —C(O)—O-aryl-R$^8$, —C(O)—NH(C$_{1-4}$alkyl-R$^9$), —C(O)—NH(aryl-R$^8$), —C(O)—N(C$_{1-4}$alkyl-R$^9$)$_2$, —SO$_2$—(C$_{1-4}$)alkyl-R$^9$, —SO$_2$-aryl-R$^8$, -cycloalkyl-R$^6$, -heterocyclyl-R$^6$, -aryl-R$^6$ and -heteroaryl-R$^6$; wherein heterocyclyl and heteroaryl are attached to the azaindole nitrogen atom in the one position via a heterocyclyl or heteroaryl ring carbon atom.

More preferably, R$^1$ is selected from the group consisting of hydrogen, —C$_{1-4}$alkyl-R$^5$, -aryl-R$^6$ and -heteroaryl-R$^6$; wherein heteroaryl is attached to the azaindole nitrogen atom in the one position via a heteroaryl ring carbon atom.

Most preferably, R$^1$ is selected from the group consisting of hydrogen, —C$_{1-4}$alkyl-R$^5$ and -naphthyl-R$^5$.

Embodiments of the present invention include compounds of Formula (I) wherein, preferably, $R^5$ is 1 to 2 substituents independently selected from the group consisting of hydrogen, —O—($C_{1-4}$)alkyl, —O—($C_{1-4}$)alkyl-OH, —O—($C_{1-4}$)alkyl-O—($C_{1-4}$)alkyl, —O—($C_{1-4}$)alkyl-$NH_2$, —O—($C_{1-4}$)alkyl-NH($C_{1-4}$alkyl), —O—($C_{1-4}$)alkyl-N($C_{1-4}$alkyl)$_2$, —O—($C_{1-4}$)alkyl-S—($C_{1-4}$)alkyl, —O—($C_{1-4}$)alkyl-$SO_2$—($C_{1-4}$)alkyl, —O—($C_{1-4}$)alkyl-$SO_2$—$NH_2$, —O—($C_{1-4}$)alkyl-$SO_2$—NH($C_{1-4}$alkyl), —O—($C_{1-4}$)alkyl-$SO_2$—N($C_{1-4}$ alkyl)$_2$, —O—C(O)H, —O—C(O)—($C_{1-4}$)alkyl, —O—C(O)—$NH_2$, —O—C(O)—NH($C_{1-4}$alkyl), —O—C(O)—N($C_{1-4}$alkyl)$_2$, —O—($C_{1-4}$)alkyl-C(O)H, —O—($C_{1-4}$)alkyl-C(O)—($C_{1-4}$)alkyl, —O—($C_{1-4}$)alkyl-$CO_2$H, —O—($C_{1-4}$)alkyl-C(O)—O—($C_{1-4}$)alkyl, —O—($C_{1-4}$)alkyl-C(O)—$NH_2$, —O—($C_{1-4}$)alkyl-C(O)—NH($C_{1-4}$alkyl), —O—($C_{1-4}$)alkyl-C(O)—N($C_{1-4}$alkyl)$_2$, —C(O)H, —C(O)—($C_{1-4}$)alkyl, —$CO_2$H, —C(O)—O—($C_{1-4}$)alkyl, —C(O)—$NH_2$, —C(NH)—$NH_2$, —C(O)—NH($C_{1-4}$alkyl), —C(O)—N($C_{1-4}$ alkyl)$_2$, —SH, —S—($C_{1-4}$)alkyl, —S—($C_{1-4}$)alkyl-S—($C_{1-4}$) alkyl, —S—($C_{1-4}$)alkyl-O—($C_{1-4}$) alkyl, —S—($C_{1-4}$)alkyl-O—($C_{1-4}$)alkyl-OH, —S—($C_{1-4}$) alkyl-O—($C_{1-4}$)alkyl-$NH_2$, —S—($C_{1-4}$)alkyl-O—($C_{1-4}$) alkyl-NH($C_{1-4}$ alkyl), —S—($C_{1-4}$)alkyl-O—($C_{1-4}$)alkyl-N($C_{1-4}$alkyl)$_2$, —S—($C_{1-4}$)alkyl-NH($C_{1-4}$alkyl), —$SO_2$—($C_{1-4}$) alkyl, —$SO_2$—$NH_2$, —$SO_2$—NH($C_{1-4}$alkyl), —$SO_2$—N($C_{1-4}$ alkyl)$_2$, —N—$R^7$, cyano, (halo)$_{1-3}$, hydroxy, nitro, oxo, -cycloalkyl-$R^6$, -heterocyclyl-$R^6$, -aryl-$R^6$ and -heteroaryl-$R^6$.

More preferably, $R^5$ is 1 to 2 substituents independently selected from the group consisting of hydrogen, —O—($C_{1-4}$) alkyl, —N—$R^7$, hydroxy and -heteroaryl-$R^6$.

Most preferably, $R^5$ is 1 to 2 substituents independently selected from the group consisting of hydrogen, —O—($C_{1-4}$) alkyl, —N—$R^7$, hydroxy, -imidazolyl-$R^6$, -triazolyl-$R^6$ and -tetrazolyl-$R^6$.

Embodiments of the present invention include compounds of Formula (I) wherein, preferably, $R^6$ is 1 to 4 substituents attached to a carbon or nitrogen atom independently selected from the group consisting of hydrogen, —$C_{1-4}$alkyl, —$C_{2-4}$alkenyl, —$C_{2-4}$alkynyl, —C(O)H, —C(O)—($C_{1-4}$)alkyl, —$CO_2$H, —C(O)—O—($C_{1-4}$)alkyl, —C(O)—$NH_2$, —C(NH)—$NH_2$, —C(O)—NH($C_{1-4}$alkyl), —C(O)—N($C_{1-4}$) alkyl)$_2$, —$SO_2$—($C_{1-4}$)alkyl, —$SO_2$—$NH_2$, —$SO_2$—NH($C_{1-4}$alkyl), —$SO_2$—N($C_{1-4}$alkyl)$_2$, —($C_{1-4}$)alkyl-N—$R^7$, —($C_{1-4}$)alkyl-(halo)$_{1-3}$, —($C_{1-4}$)alkyl-OH, -aryl-$R^8$, —($C_{1-4}$) alkyl-aryl-$R^8$ and —($C_{1-4}$)alkyl-heteroaryl-$R^8$;

with the proviso that, when $R^6$ is attached to a carbon atom, $R^6$ is further selected from the group consisting of —$C_{1-4}$ alkoxy, —($C_{1-4}$)alkoxy-(halo)$_{1-3}$, —SH, —S—($C_{1-4}$)alkyl, —N—$R^7$, cyano, halo, hydroxy, nitro, oxo and -heteroaryl-$R^8$.

More preferably, $R^6$ is hydrogen.

Embodiments of the present invention include compounds of Formula (I) wherein, preferably, $R^7$ is 2 substituents independently selected from the group consisting of hydrogen, —$C_{1-4}$alkyl, —$C_{2-4}$alkenyl, —$C_{2-4}$alkynyl, —($C_{1-4}$)alkyl-OH, —($C_{1-4}$)alkyl-O—($C_{1-4}$)alkyl, —($C_{1-4}$)alkyl-$NH_2$, —($C_{1-4}$)alkyl-NH($C_{1-4}$alkyl), —($C_{1-4}$)alkyl-N($C_{1-4}$alkyl)$_2$, —($C_{1-4}$)alkyl-S—($C_{1-4}$)alkyl, —C(O)H, —C(O)—($C_{1-4}$) alkyl, —C(O)—O—($C_{1-4}$)alkyl, —C(O)—$NH_2$, —C(O)—NH($C_{1-4}$alkyl), —C(O)—N($C_{1-4}$alkyl)$_2$, —$SO_2$—($C_{1-4}$) alkyl, —$SO_2$—$NH_2$, —$SO_2$—NH($C_{1-4}$alkyl), —$SO_2$—N($C_{1-4}$alkyl)$_2$, —C(N)—$NH_2$, -cycloalkyl-$R^8$, —($C_{1-4}$)alkyl-heterocyclyl-$R^8$, -aryl-$R^8$, —($C_{1-4}$)alkyl-aryl-$R^8$ and —($C_{1-4}$) alkyl-heteroaryl-$R^8$.

More preferably, $R^7$ is 2 substituents independently selected from the group consisting of hydrogen, —$C_{1-4}$alkyl, —C(O)H, —C(O)—($C_{1-4}$)alkyl, —C(O)—O—($C_{1-4}$)alkyl, —$SO_2$—$NH_2$, —$SO_2$—NH($C_{1-4}$alkyl) and —$SO_2$—N($C_{1-4}$ alkyl)$_2$.

Embodiments of the present invention include compounds of Formula (I) wherein, preferably, $R^8$ is 1 to 4 substituents attached to a carbon or nitrogen atom independently selected from the group consisting of hydrogen, —$C_{1-4}$alkyl, —($C_{1-4}$) alkyl-(halo)$_{1-3}$ and —($C_{1-4}$)alkyl-OH;

with the proviso that, when $R^8$ is attached to a carbon atom, $R^8$ is further selected from the group consisting of —$C_{1-4}$ alkoxy, —$NH_2$, —NH($C_{1-4}$alkyl), —N($C_{1-4}$alkyl)$_2$, cyano, halo, —($C_{1-4}$)alkoxy-(halo)$_{1-3}$, hydroxy and nitro.

More preferably, $R^8$ is hydrogen.

Embodiments of the present invention include compounds of Formula (I) wherein, preferably, $R^9$ is 1 to 2 substituents independently selected from the group consisting of hydrogen, —$C_{1-4}$alkoxy, —$NH_2$, —NH($C_{1-4}$alkyl), —N($C_{1-4}$ alkyl)$_2$, cyano, (halo)$_{1-3}$, hydroxy and nitro.

More preferably, $R^9$ is hydrogen.

Embodiments of the present invention include compounds of Formula (I) wherein, preferably, $R^2$ is one substituent attached to a carbon or nitrogen atom selected from the group consisting of hydrogen, —$C_{1-4}$alkyl-$R^5$, —$C_{2-4}$alkenyl-$R^5$, —$C_{2-4}$alkynyl-$R^5$, —C(O)H, —C(O)—($C_{1-4}$)alkyl-$R^9$, —C(O)—$NH_2$, —C(O)—NH($C_{1-4}$alkyl-$R^9$), —C(O)—N($C_{1-4}$alkyl-$R^9$)$_2$, —C(O)—NH(aryl-$R^8$), —C(O)-cycloalkyl-$R^8$, —C(O)-heterocyclyl-$R^8$, —C(O)-aryl-$R_3$, —C(O)-heteroaryl-$R^8$, —$CO_2$H, —C(O)—O—($C_{1-4}$)alkyl-$R^9$, —C(O)—O-aryl-$R^8$, —$SO_2$—($C_{1-4}$)alkyl-$R^9$, —$SO_2$-aryl-$R^8$, -cycloalkyl-$R^6$, -aryl-$R^6$ and —($C_{1-4}$)alkyl-N—$R^7$;

with the proviso that, when $R^2$ is attached to a carbon atom, $R^2$ is further selected from the group consisting of —$C_{1-4}$ alkoxy-$R^5$, —N—$R^7$, cyano, halogen, hydroxy, nitro, oxo, -heterocyclyl-$R^6$ and -heteroaryl-$R^6$.

More preferably, $R^2$ is one substituent attached to a carbon or nitrogen atom selected from the group consisting of hydrogen, —$C_{1-4}$alkyl-$R^5$, —$C_{2-4}$alkenyl-$R^5$, —$C_{2-4}$alkynyl-$R^5$, —$CO_2$H, —C(O)—O—($C_{1-4}$)alkyl-$R^9$, -cycloalkyl-$R^6$, -aryl-$R^6$ and —($C_{1-4}$)alkyl-N—$R^7$;

with the proviso that, when $R^2$ is attached to a nitrogen atom, a quaternium salt is not formed; and, with the proviso that, when $R^2$ is attached to a carbon atom, $R^2$ is further selected from the group consisting of —$C_{1-4}$alkoxy-$R^5$, —N—$R^7$, cyano, halogen, hydroxy, nitro, oxo, -heterocyclyl-$R^6$ and -heteroaryl-$R^6$.

Most preferably, $R^2$ is one substituent attached to a carbon or nitrogen atom selected from the group consisting of hydrogen, —$C_{1-4}$alkyl-$R^5$ and -aryl-$R^6$; with the proviso that, when $R^2$ is attached to a nitrogen atom, a quaternium salt is not formed; and, with the proviso that when $R^2$ is attached to a carbon atom, $R^2$ is further selected from the group consisting of —N—$R^7$, halogen, hydroxy and -heteroaryl-$R^6$.

Embodiments of the present invention include compounds of Formula (I) wherein, preferably, $R^3$ is 1 to 3 substituents attached to a carbon atom independently selected from the group consisting of hydrogen, —$C_{1-4}$alkyl-$R^{10}$, —$C_{2-4}$alkenyl-$R^{10}$, —$C_{2-4}$alkynyl-$R^{10}$, —$C_{1-4}$alkoxy-$R^{10}$, —C(O)H, —C(O)—($C_{1-4}$)alkyl-$R^9$, —C(O)—$NH_2$, —C(O)—NH($C_{1-4}$ alkyl-$R^9$), —C(O)—N($C_{1-4}$alkyl-$R^9$)$_2$, —C(O)-cycloalkyl-$R^8$, —C(O)-heterocyclyl-$R^8$, —C(O)-aryl-$R^8$, —C(O)-heteroaryl-$R^8$, —C(NH)—$NH_2$, —$CO_2$H, —C(O)—O—($C_{1-4}$)alkyl-$R^9$, —C(O)—O-aryl-$R^8$, —$SO_2$—($C_{1-8}$)alkyl-$R^9$, —$SO_2$-aryl-$R^8$, —N—$R^7$, —($C_{1-4}$) alkyl-N—$R^7$, cyano, halogen, hydroxy, nitro, -cycloalkyl-$R^8$, -heterocyclyl-$R^8$, -aryl-$R^8$ and -heteroaryl-$R^8$.

More preferably, $R^3$ is one substituent attached to a carbon atom selected from the group consisting of hydrogen, —$C_{1-4}$alkyl-$R^{10}$, —$C_{2-4}$alkenyl-$R^{10}$, —$C_{2-4}$alkynyl-$R^{10}$, —$C_{1-4}$alkoxy-$R^{10}$, —C(O)H, —$CO_2$H, —$NH_2$, —NH($C_{1-4}$alkyl), —N($C_{1-4}$alkyl)$_2$, cyano, halogen, hydroxy and nitro.

Most preferably, $R^3$ is one substituent attached to a carbon atom selected from the group consisting of hydrogen, —$C_{1-4}$alkyl-$R^{10}$, —$NH_2$, —NH($C_{1-4}$alkyl), —N($C_{1-4}$alkyl)$_2$, halogen and hydroxy.

Embodiments of the present invention include compounds of Formula (I) wherein, $R^4$ is 1 to 4 substituents attached to a carbon atom independently selected from the group consisting of hydrogen, —$C_{1-4}$alkyl-$R^{10}$, —$C_{2-4}$alkenyl-$R^{10}$, —$C_{2-4}$alkynyl-$R^{10}$, —$C_{1-4}$alkoxy-$R^{10}$, —C(O)H, —C(O)—($C_{1-4}$)alkyl-$R^9$, —C(O)—$NH_2$, —C(O)—NH($C_{1-4}$alkyl-$R^9$), —C(O)—N($C_{1-4}$alkyl-$R^9$)$_2$, —C(O)-cycloalkyl-$R^8$, —C(O)-heterocyclyl-$R^8$, —C(O)-aryl-$R^8$, —C(O)-heteroaryl-$R^8$, —C(NH)—$NH_2$, —$CO_2$H, —C(O)—O—($C_{1-4}$)alkyl-$R^9$, —C(O)—O-aryl-$R^8$, —SH, —S—($C_{1-4}$)alkyl-$R^{10}$, —$SO_2$—($C_{1-4}$)alkyl-$R^9$, —$SO_2$-aryl-$R^8$, —$SO_2$—$NH_2$, —$SO_2$—NH($C_{1-4}$alkyl-$R^9$), —$SO_2$—N($C_{1-4}$alkyl-$R^9$)$_2$, —N—$R^7$, cyano, halogen, hydroxy, nitro, -cycloalkyl-$R^8$, -heterocyclyl-$R^8$, -aryl-$R^8$ and -heteroaryl-$R^8$.

Preferably, $R^4$ is 1 to 4 substituents attached to a carbon atom independently selected from the group consisting of hydrogen, —$C_{1-4}$alkyl-$R^{10}$, —$C_{2-4}$alkenyl-$R^{10}$, —$C_{2-4}$alkynyl-$R^{10}$, —$C_{1-4}$alkoxy-$R^{10}$, —C(O)H, —$CO_2$H, —$NH_2$, —NH($C_{1-4}$alkyl), —N($C_{1-4}$alkyl)$_2$, cyano, halogen, hydroxy, nitro, -cycloalkyl, -heterocyclyl, -aryl and -heteroaryl.

More preferably, $R^4$ is 1 to 4 substituents attached to a carbon atom independently selected from the group consisting of hydrogen, $C_{1-4}$alkyl-$R^{10}$, $C_{1-4}$alkoxy-$R^{10}$, —$NH_2$, —NH($C_{1-4}$alkyl), —N($C_{1-4}$alkyl)$_2$, halogen and hydroxy.

Most preferably, $R^4$ is 1 to 4 substituents attached to a carbon atom independently selected from the group consisting of hydrogen, $C_{1-4}$alkyl-$R^{10}$, $C_{1-4}$alkoxy-$R^{10}$, —$NH_2$, —NH($C_{1-4}$alkyl), —N($C_{1-4}$alkyl)$_2$, chlorine, fluorine and hydroxy.

Embodiments of the present invention include compounds of Formula (I) wherein, preferably, $R^{10}$ is 1 to 2 substituents independently selected from the group consisting of hydrogen, —$NH_2$, —NH($C_{1-4}$alkyl), —N($C_{1-4}$alkyl)$_2$, cyano, (halo)$_{1-3}$, hydroxy, nitro and oxo.

More preferably, $R^{10}$ is 1 to 2 substituents independently selected from the group consisting of hydrogen and (halo)$_{1-3}$.

Most preferably, $R^{10}$ is 1 to 2 substituents independently selected from the group consisting of hydrogen and (fluoro)$_3$.

Embodiments of the present invention include compounds of Formula (I) wherein, preferably, Y and Z are independently selected from the group consisting of O, S, (H,OH) and (H,H); with the proviso that one of Y and Z is O and the other is selected from the group consisting of O, S, (H,OH) and (H,H).

More preferably, Y and Z are independently selected from the group consisting of O and (H,H); with the proviso that one of Y and Z is O, and the other is selected from the group consisting of O and (H,H).

Most preferably, Y and Z are independently selected from O.

Exemplified compounds of Formula (I) include compounds selected from Formula (Ia):

TABLE 1

Formula (Ia)

wherein R, $R^1$, $R^2$, $R^3$ and $R^4$ are dependently selected from:

| Cpd | $R^1$ | $R^3$ | R | $R^2$ | $R^4$ |
|---|---|---|---|---|---|
| 1 | $CH_3O(CH_2)_3$ | H | Ph | H | 2-$OCH_3$; |
| 2 | $CH_3O(CH_2)_3$ | H | Ph | H | 2-Cl; |

The compounds of the present invention may also be present in the form of pharmaceutically acceptable salts. For use in medicine, the salts of the compounds of this invention refer to non-toxic "pharmaceutically acceptable salts" (*Ref. International J. Pharm.*, 1986, 33, 201-217; *J. Pharm.Sci.*, 1997 (January), 66, 1, 1). Other salts may, however, be useful in the preparation of compounds according to this invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benezenesulfonic, oxalic, pamoic, 2-naphthalenesulfonic, p-toluenesulfonic, cyclohexanesulfamic, salicylic, saccharinic or trifluoroacetic acid. Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the subject. Conventional procedures for the selection and preparation of suitable prodrug derivatives are described, for example, in "*Design of Prodrugs*", ed. H. Bundgaard, Elsevier, 1985.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry,* ed. J. F. W. McOmie, Plenum Press, 1973; and T. W. Greene & P. G. M. Wuts, *Protective Groups in Organic Synthesis,* John Wiley & Sons, 1991. The protecting groups may be removed at a convenient subsequent stage using methods known in the art.

Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

The term "independently" means that when a group is substituted with more than one substituent that the substituents may be the same or different. The term "dependently" means that the substituents are specified in an indicated combination of structure variables.

Unless specified otherwise, the term "alkyl" refers to a saturated straight or branched chain consisting solely of 1-8 hydrogen substituted carbon atoms; preferably, 1-6 hydrogen substituted carbon atoms; and, most preferably, 1-4 hydrogen substituted carbon atoms. The term "alkenyl" refers to a partially unsaturated straight or branched chain consisting solely of 2-8 hydrogen substituted carbon atoms that contains at least one double bond. The term "alkynyl" refers to a partially unsaturated straight or branched chain consisting solely of 2-8 hydrogen substituted carbon atoms that contains at least one triple bond. The term "alkoxy" refers to —O-alkyl, where alkyl is as defined supra. The term "hydroxyalkyl" refers to radicals wherein the alkyl chain terminates with a hydroxy radical of the formula HO-alkyl, where alkyl is as defined supra. $C_{1-8}$alkoxy refers to a —O-alkyl wherein the alkyl has one to eight carbon atoms. $C_{1-8}$alkoxy-$R_{10}$ refers to a —O-alkyl further substituted with $R_{10}$ on the alkyl. Alkyl, alkenyl and alkynyl chains are optionally substituted within the alkyl chain or on a terminal carbon atom.

The term "cycloalkyl" refers to a saturated or partially unsaturated monocyclic alkyl ring consisting of 3-8 hydrogen substituted carbon atoms or a saturated or partially unsaturated bicyclic ring consisting of 9 or 10 hydrogen substituted carbon atoms. Examples include, and are not limited to, cyclopropyl, cyclopentyl, cyclohexyl or cycloheptyl.

The term "heterocyclyl" refers to a saturated or partially unsaturated ring having five members of which at least one member is a N, O or S atom and which optionally contains one additional O atom or one, two or three additional N atoms, wherein at most two nitrogen atoms are adjacent; a saturated or partially unsaturated ring having six members of which one, two or three members are a N atom, wherein at most two nitrogen atoms are adjacent; or, a saturated or partially unsaturated bicyclic ring having nine or ten members of which at least one member is a N, O or S atom and which optionally contains one, two or three additional N atoms, wherein at most two nitrogen atoms are adjacent. Examples include, and are not limited to, pyrrolinyl, pyrrolidinyl, 1,3-dioxolanyl, imidazolinyl, imidazolidinyl, pyrazolinyl, pyrazolidinyl, piperidinyl, morpholinyl or piperazinyl.

The term "aryl" refers to an aromatic monocyclic ring containing 6 hydrogen substituted carbon atoms, an aromatic bicyclic ring system containing 10 hydrogen substituted carbon atoms or an aromatic tricyclic ring system containing 14 hydrogen substituted carbon atoms. Examples include, and are not limited to, phenyl, naphthalenyl or anthracenyl.

The term "heteroaryl" refers to an aromatic monocyclic ring system containing five members of which at least one member is a N, O or S atom and which optionally contains one, two or three additional N atoms, wherein at most two nitrogen atoms are adjacent; an aromatic monocyclic ring having six members of which one, two or three members are a N atom, wherein at most two nitrogen atoms are adjacent; an aromatic bicyclic ring having nine members of which at least one member is a N, O or S atom and which optionally contains one, two or three additional N atoms, wherein at most two nitrogen atoms are adjacent; an aromatic bicyclic ring having ten members of which one, two or three members are a N atom, wherein at most two nitrogen atoms are adjacent; or, an aromatic tricyclic ring system containing 13 or 14 members of which at least one member is a N, O or S atom and which optionally contains one, two or three additional N atoms, wherein at most two nitrogen atoms are adjacent.

The "carboxyl" as used herein refers to the organic radical terminal group: R—C(O)OH.

Whenever the term "alkyl" or "aryl" or either of their prefix roots appear in a name of a substituent (e.g., aralkyl, alkylamino) it shall be interpreted as including those limitations given above for "alkyl" and "aryl." Designated numbers of carbon atoms (e.g., $C_1$-$C_6$) shall refer independently to the number of carbon atoms in an alkyl or cycloalkyl moiety or to the alkyl portion of a larger substituent in which alkyl appears as its prefix root.

Unless indicated otherwise, under standard nomenclature rules used throughout this disclosure, the terminal portion of the designated side chain is described first, followed by the adjacent functionality toward the point of attachment. Thus, for example, a "phenyl($C_{1-6}$)alkylamido($C_{1-6}$)alkyl" substituent refers to a group of the formula:

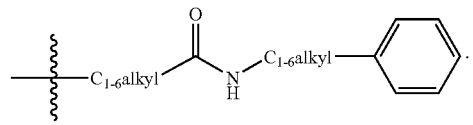

When the substituent's point of attachment is not otherwise clear, a dashed line is used to indicate the point of attachment, followed by the adjacent functionality and ending with the terminal functionality such as, for example, —($C_{1-4}$)alkyl-NH—($C_{1-4}$)alkyl.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

An embodiment of the invention is a pharmaceutical composition comprising a pharmaceutically acceptable carrier and any of the compounds described above. Illustrative of the invention is a pharmaceutical composition made by mixing any of the compounds described above and a pharmaceutically acceptable carrier. Another illustration of the invention is a process for making a pharmaceutical composition comprising mixing any of the compounds described above and a pharmaceutically acceptable carrier. Further illustrative of the present invention are pharmaceutical compositions comprising one or more compounds of this invention in association with a pharmaceutically acceptable carrier.

As used herein, the term "composition" is intended to encompass a product comprising the specified ingredients in the specified amounts, as well as any product which results, directly or indirectly, from combinations of the specified ingredients in the specified amounts.

The compounds of the present invention are selective kinase or dual-kinase inhibitors useful in a method for treating or ameliorating a kinase or dual-kinase mediated disorder. In particular, the kinase is selected from protein kinase C or glycogen synthase kinase-3. More particularly, the kinase is selected from protein kinase C α, protein kinase C β-II, protein kinase C γ or glycogen synthase kinase-3β.

Protein Kinase C Isoforms

Protein kinase C is known to play a key role in intracellular signal transduction (cell-cell signaling), gene expression and in the control of cell differentiation and growth. The PKC family is composed of twelve isoforms that are further classified into 3 subfamilies: the calcium dependent classical PKC isoforms alpha (α), beta-I (β-I), beta-II (β-II) and gamma (γ); the calcium independent PKC isoforms delta (δ), epsilon (ε), eta (η), theta (θ) and mu (μ); and, the atypical PKC isoforms zeta (ζ), lambda (λ) and iota (ι).

Certain disease states tend to be associated with elevation of particular PKC isoforms. The PKC isoforms exhibit distinct tissue distribution, subcellular localization and activation-dependent cofactors. For example, the α and β isoforms of PKC are selectively induced in vascular cells stimulated with agonists such as vascular endothelial growth factor (VEGF) (P. Xia, et al., *J. Clin. Invest.*, 1996, 98, 2018) and have been implicated in cellular growth, differentiation, and vascular permeability (H. Ishii, et al., *J. Mol. Med.*, 1998, 76, 21). The elevated blood glucose levels found in diabetes leads to an isoform-specific elevation of the β-II isoform in vascular tissues (Inoguchi, et al., *Proc. Natl. Acad. Sci. USA*, 1992, 89, 11059-11065). A diabetes-linked elevation of the β isoform in human platelets has been correlated with their altered response to agonists (Bastyr III, E. J. and Lu, J., *Diabetes*, 1993, 42, (Suppl. 1) 97A). The human vitamin D receptor has been shown to be selectively phosphorylated by PKCβ. This phosphorylation has been linked to alterations in the functioning of the receptor (Hsieh, et al., *Proc. Natl. Acad. Sci. USA*, 1991, 88, 9315-9319; Hsieh, et al., *J. Biol. Chem.*, 1993, 268, 15118-15126). In addition, the work has shown that the β-II isoform is responsible for erythroleukemia cell proliferation while the α isoform is involved in megakaryocyte differentiation in these same cells (Murray, et al., *J. Biol. Chem.*, 1993, 268, 15847-15853).

Cardiovascular Diseases

PKC activity plays an important role in cardiovascular diseases. Increased PKC activity in the vasculature has been shown to cause increased vasoconstriction and hypertension (Bilder, G. E., et al., *J. Pharmacol. Exp. Ther.*, 1990, 252, 526-530). PKC inhibitors block agonist-induced smooth muscle cell proliferation (Matsumoto, H. and Sasaki, Y., *Biochem. Biophys. Res. Commun.*, 1989, 158, 105-109). PKC β triggers events leading to induction of Egr-1 (Early Growth Factor-1) and tissue factor under hypoxic conditions (as part of the oxygen deprivation-mediated pathway for triggering procoagulant events) (Yan, S-F, et al., *J. Biol. Chem.*, 2000, 275, 16, 11921-11928). PKC β is suggested as a mediator for production of PAI-1 (Plaminogen Activator Inhibitor-1) and is implicated in the development of thrombosis and atherosclerosis (Ren, S, et al., *Am. J. Physiol.*, 2000, 278, (4, Pt. 1), E656-E662). PKC inhibitors are useful in treating cardiovascular ischemia and improving cardiac function following ischemia (Muid, R. E., et al., *FEBS Lett.*, 1990, 293, 169-172; Sonoki, H. et al., *Kokyu-To Junkan*, 1989, 37, 669-674). Elevated PKC levels have been correlated with an increased platelet function response to agonists (Bastyr III, E. J. and Lu, J., *Diabetes*, 1993, 42, (Suppl. 1) 97A). PKC has been implicated in the biochemical pathway in the platelet-activating factor (PAF) modulation of microvascular permeability (Kobayashi, et al., *Amer. Phys. Soc.*, 1994, H1214- H1220). PKC inhibitors affect agonist-induced aggregation in platelets (Toullec, D., et al., *J. Biol. Chem.*, 1991, 266, 15771-15781). Accordingly, PKC inhibitors may be indicated for use in treating cardiovascular disease, ischemia, thrombotic conditions, atherosclerosis and restenosis.

Diabetes

Excessive activity of PKC has been linked to insulin signaling defects and therefore to the insulin resistance seen in Type II diabetes (Karasik, A., et al., *J. Biol. Chem.*, 1990, 265, 10226-10231; Chen, K. S., et al., *Trans. Assoc. Am. Physicians*, 1991, 104, 206-212; Chin, J. E., et al., *J. Biol. Chem.*, 1993, 268, 6338-6347).

Diabetes-Associated Disorders

Studies have demonstrated an increase in PKC activity in tissues known to be susceptible to diabetic complications when exposed to hyperglycemic conditions (Lee, T-S., et al., *J. Clin. Invest*, 1989, 83, 90-94; Lee, T-S., et al., *Proc. Natl. Acad. Sci. USA*, 1989, 86, 5141-5145; Craven, P. A. and DeRubertis, F. R., *J. Clin. Invest.*, 1989, 87, 1667-1675; Wolf, B. A., et al., *J. Clin. Invest.*, 1991, 87, 31-38; Tesfamariam, B., et al., *J. Clin. Invest.*, 1991, 87, 1643-1648). For example, activation of the PKC-β-II isoform plays an important role in diabetic vascular complications such as retinopathy (Ishii, H., et al., *Science*, 1996, 272, 728-731) and PKCβ has been implicated in development of the cardiac hypertrophy associated with heart failure (X. Gu, et al., *Circ. Res.*, 1994, 75, 926; R. H. Strasser, et al., *Circulation*, 1996, 94, 1551). Overexpression of cardiac PKCβII in transgenic mice caused cardiomyopathy involving hypertrophy, fibrosis and decreased left ventricular function (H. Wakasaki, et al., *Proc. Natl. Acad. Sci. USA*, 1997, 94, 9320).

Inflammatory Diseases

PKC inhibitors block inflammatory responses such as the neutrophil oxidative burst, CD3 down-regulation in T-lymphocytes and phorbol-induced paw edema (Twoemy, B., et al., *Biochem. Biophys. Res. Commun.*, 1990, 171, 1087-1092; Mulqueen, M. J., et al. *Agents Actions*, 1992, 37, 85-89). PKC β has an essential role in the degranulation of bone marrow-derived mast cells, thus affecting cell capacity to produce IL-6 (Interleukin-6) (Nechushtan, H., et al., *Blood*, 2000 (March), 95, 5, 1752-1757). PKC plays a role in enhanced ASM (Airway Smooth Muscle) cell growth in rat models of two potential risks for asthma: hyperresponsiveness to contractile agonists and to growth stimuli (Ren, S, et al., *Am. J. Physiol.*, 2000, 278, (4, Pt. 1), E656-E662). PKC β-1 overexpression augments an increase in endothelial permeability, suggesting an important function in the regulation of the endothelial barrier (Nagpala, P. G., et al., *J. Cell Physiol.*, 1996, 2, 249-55). PKC β mediates activation of neutrophil NADPH oxidase by PMA and by stimulation of Fcγ receptors in neutrophils (Dekker, L. V., et al., *Biochem. J.*, 2000, 347, 285-289). Thus, PKC. inhibitors may be indicated for use in treating inflammation and asthma.

Immunological Disorders

PKC may be useful in treating or ameliorating certain immunological disorders. While one study suggests that HCMV (Human Cytomegalovirus) inhibition is not correlated with PKC inhibition (Slater, M. J., et al., *Biorg. & Med. Chem.*, 1999, 7, 1067-1074), another study showed that the PKC signal transduction pathway synergistically interacted with the cAMP-dependent PKA pathway to activate or increase HIV-1 transcription and viral replication and was abrogated with a PKC inhibitor (Rabbi, M. F., et al., *Virology*, 1998 (June 5), 245, 2, 257-69). Therefore, an immunological disorder may be treated or ameliorated as a function of the affected underlying pathway's response to up- or down-regulation of PKC.

PKC β deficiency also results in an immunodeficiency characterized by impaired humoral immune responses and a reduced B cell response, similar to X-linked immunodeficiency in mice, playing an important role in antigen receptor-mediated signal transduction (Leitges, M., et al., *Science (Wash., D.C.)*, 1996, 273, 5276, 788-789). Accordingly, transplant tissue rejection may be ameliorated or prevented by suppressing the immune response using a PKC β inhibitor.

Dermatological Disorders

Abnormal activity of PKC has been linked to dermatological disorders characterized by abnormal proliferation of keratinocytes, such as psoriasis (Horn, F., et al., *J. Invest. Dermatol.*, 1987, 88, 220-222; Raynaud, F. and Evain-Brion, D., *Br. J. Dermatol.*, 1991, 124, 542-546). PKC inhibitors have been shown to inhibit keratinocyte proliferation in a dose-dependent manner (Hegemann, L., et al., *Arch. Dermatol. Res.*, 1991, 283, 456-460; Bollag, W. B., et al., *J. Invest. Dermatol.*, 1993, 100, 240-246).

Oncological Disorders

PKC activity has been associated with cell growth, tumor promotion and cancer (Rotenberg, S. A. and Weinstein, I. B., *Biochem. Mol. Aspects Sel. Cancer*, 1991, 1, 25-73; Ahmad, et al., *Molecular Pharmacology*, 1993, 43, 858-862); PKC inhibitors are known to be effective in preventing tumor growth in animals (Meyer, T., et al., *Int. J. Cancer*, 1989, 43, 851-856; Akinagaka, S., et al., *Cancer Res.*, 1991, 51, 4888-4892). PKC β-1 and β-2 expression in differentiated HD3 colon carcinoma cells blocked their differentiation, enabling them to proliferate in response to basic FGF (Fibroblast Growth Factor) like undifferentiated cells, increasing their growth rate and activating several MBP (Myelin-Basic Protein) kinases, including p57 MAP (Mitogen-Activated Protein) kinase (Sauma, S., et al., *Cell Growth Differ.*, 1996, 7, 5, 587-94). PKC α inhibitors, having an additive therapeutic effect in combination with other anti-cancer agents, inhibited the growth of lymphocytic leukemia cells (Konig, A., et al., *Blood*, 1997, 90, 10, Suppl. 1 Pt. 2). PKC inhibitors enhanced MMC (Mitomycin-C) induced apoptosis in a time-dependent fashion in a gastric cancer cell-line, potentially indicating use as agents for chemotherapy-induced apoptosis (Danso, D., et al., *Proc. Am. Assoc. Cancer Res.*, 1997, 38, 88 Meet., 92). Therefore, PKC inhibitors may be indicated for use in ameliorating cell and tumor growth, in treating or ameliorating cancers (such as leukemia or colon cancer) and as adjuncts to chemotherapy.

PKC α (by enhancing cell migration) may mediate some proangiogenic effects of PKC activation while PKC δ may direct antiangiogenic effects of overall PKC activation (by inhibiting cell growth and proliferation) in capillary endothelial cells, thus regulating endothelial proliferation and angiogenesis (Harrington, E. O., et al., *J. Biol. Chem.*, 1997, 272, 11, 7390-7397). PKC inhibitors inhibit cell growth and induce apoptosis in human glioblastoma cell lines, inhibit the growth of human astrocytoma xenografts and act as radiation sensitizers in glioblastoma cell lines (Begemann, M., et al., *Anticancer Res. (Greece)*, 1998 (July-August), 18, 4A, 2275-82). PKC inhibitors, in combination with other anti-cancer agents, are radiation and chemosensitizers useful in cancer therapy (Teicher, B. A., et al., *Proc. Am. Assoc. Cancer Res.*, 1998, 39, 89 Meet., 384). PKC β inhibitors (by blocking the MAP kinase signal transduction pathways for VEGF (Vascular Endothelial Growth Factor) and bFGF (basic Fibrinogen Growth Factor) in endothelial cells), in a combination regimen with other anti-cancer agents, have an anti-angiogenic and antitumor effect in a human T98G glioblastoma multiforme xenograft model (Teicher, B. A., et al., *Clinical Cancer Research*, 2001 (March), 7, 634-640). Accordingly, PKC inhibitors may be indicated for use in ameliorating angiogenesis and in treating or ameliorating cancers (such as breast, brain, kidney, bladder, ovarian or colon cancers) and as adjuncts to chemotherapy and radiation therapy.

Central Nervous System Disorders

PKC activity plays a central role in the functioning of the central nervous system (CNS) (Huang, K. P., *Trends Neurosci.*, 1989, 12, 425-432) and PKC is implicated in Alzheimer's disease (Shimohama, S., et al., *Neurology*, 1993, 43, 1407-1413) and inhibitors have been shown to prevent the damage seen in focal and central ischemic brain injury and brain edema (Hara, H., et al., *J. Cereb. Blood Flow Metab.*, 1990, 10, 646-653; Shibata, S., et al., *Brain Res.*, 1992, 594, 290-294). Accordingly, PKC inhibitors may be indicated for use in treating Alzheimer's disease and in treating neurotraumatic and ischemia-related diseases.

The long-term increase in PKC γ (as a component of the phosphoinositide $2^{nd}$ messenger system) and muscarinic acetylcholine receptor expression in an amygdala-kindled rat model has been associated with epilepsy, serving as a basis for the rat's permanent state of hyperexcitability (Beldhuis, H. J. A., et al., *Neuroscience*, 1993, 55, 4, 965-73). Therefore, PKC inhibitors may be indicated for use in treating epilepsy.

The subcellular changes in content of the PKC γ and PKC β-II isoenzymes for animals in an in-vivo thermal hyperalgesia model suggests that peripheral nerve injury contributes to the development of persistent pain (Miletic, V., et al., *Neurosci. Lett.*, 2000, 288, 3, 199-202). Mice lacking PKC γ display normal responses to acute pain stimuli, but almost completely fail to develop a neuropathic pain syndrome after partial sciatic nerve section (Chen, C., et al., *Science (Wash., D.C.)*, 1997, 278, 5336, 279-283). PKC modulation may thus be indicated for use in treating chronic pain and neuropathic pain.

PKC has demonstrated a role in the pathology of conditions such as, but not limited to, cardiovascular diseases, diabetes, diabetes-associated disorders, inflammatory diseases, immunological disorders, dermatological disorders, oncological disorders and central nervous system disorders.

Glycogen Synthase Kinase-3

Glycogen synthase kinase-3 (GSK-3) is a serine/threonine protein kinase composed of two isoforms (α and β) which are encoded by distinct genes. GSK-3 is one of several protein kinases which phosphorylate glycogen synthase (GS) (Embi, et al., *Eur. J. Biochem*, 1980, 107, 519-527). The α and β isoforms have a monomeric structure of 49 and 47 kD respectively and are both found in mammalian cells. Both isoforms phosphorylate muscle glycogen synthase (Cross, et al., *Biochemical Journal*, 1994, 303, 21-26) and these two isoforms show good homology between species (human and rabbit GSK-3α are 96% identical).

Diabetes

Type II diabetes (or Non-Insulin Dependent Diabetes Mellitus, NIDDM) is a multifactorial disease. Hyperglycemia is due to insulin resistance in the liver, muscle and other tissues coupled with inadequate or defective secretion of insulin from pancreatic islets. Skeletal muscle is the major site for insulin-stimulated glucose uptake and in this tissue glucose removed from the circulation is either metabolised through glycolysis and the TCA (tricarboxylic acid) cycle or stored as glycogen. Muscle glycogen deposition plays the more important role in glucose homeostasis and Type II diabetic subjects have defective muscle glycogen storage. The stimulation of glycogen synthesis by insulin in skeletal muscle results from the dephosphorylation and activation of glycogen synthase (Villar-Palasi C. and Larner J., *Biochim. Biophys. Acta*, 1960, 39, 171-173, Parker P. J., et al., *Eur. J. Biochem.*, 1983, 130, 227-234, and Cohen P., *Biochem. Soc. Trans.*, 1993, 21, 555-567). The phosphorylation and dephosphorylation of GS are mediated by specific kinases and phosphatases. GSK-3 is responsible for phosphorylation and deactivation of GS, while glycogen bound protein phosphatase 1 (PP1G) dephosphorylates and activates GS. Insulin both inactivates GSK-3 and activates PP1G (Srivastava A. K. and Pandey S. K., *Mol. and Cellular Biochem.*, 1998, 182, 135-141).

Studies suggest that an increase in GSK-3 activity might be important in Type II diabetic muscle (Chen, et al., *Diabetes*, 1994, 43, 1234-1241). Overexpression of GSK-3β and constitutively active GSK-3β (S9A, S9e) mutants in HEK-293 cells resulted in suppression of glycogen synthase activity (Eldar-Finkelman, et al., *PNAS*, 1996, 93, 10228-10233) and overexpression of GSK-3β in CHO cells, expressing both insulin receptor and insulin receptor substrate 1 (IRS-1) resulted in impairment of insulin action (Eldar-Finkelman and Krebs, *PNAS*, 1997, 94, 9660-9664). Recent evidence for the involvement of elevated GSK-3 activity and the development of insulin resistance and Type II diabetes in adipose tissue has emerged from studies undertaken in diabetes and obesity prone C57BL/6J mice (Eldar-Finkelman, et al., *Diabetes*, 1999, 48, 1662-1666).

Dermatological Disorders

The finding that transient β-catenin stabilization may play a role in hair development (Gat, et al., *Cell*, 1998, 95, 605-614) suggests that GSK-3 inhibitors could also be used in the treatment of baldness.

Inflammatory Diseases

Studies on fibroblasts from the GSK-3β knockout mouse indicate that inhibition of GSK-3 may be useful in treating inflammatory disorders or diseases through the negative regulation of NFkB activity (Hoeflich K. P., et al., *Nature*, 2000, 406, 86-90).

Central Nervous System Disorders

In addition to modulation of glycogen synthase activity, GSK-3 also plays an important role in the CNS disorders. GSK-3 inhibitors may be of value as neuroprotectants in the treatment of acute stroke and other neurotraumatic injuries (Pap and Cooper, *J. Biol. Chem.*, 1998, 273, 19929-19932). Lithium, a low mM inhibitor of GSK-3, has been shown to protect cerebellar granule neurons from death (D'Mello, et al., *Exp. Cell Res.*, 1994, 211, 332-338) and chronic lithium treatment has demonstrable efficacy in the middle cerebral artery occlusion model of stroke in rodents (Nonaka and Chuang, *Neuroreport*, 1998, 9(9), 2081-2084).

Tau and β-catenin, two known in vivo substrates of GSK-3, are of direct relevance in consideration of further aspects of the value of GSK-3 inhibitors in relation to treatment of chronic neurodegenerative conditions. Tau hyperphosphorylation is an early event in neurodegenerative conditions such as Alzheimer's disease and is postulated to promote microtubule disassembly. Lithium has been reported to reduce the phosphorylation of tau, enhance the binding of tau to microtubules and promote microtubule assembly through direct and reversible inhibition of GSK-3 (Hong M. et al *J. Biol. Chem.*, 1997, 272(40), 25326-32). β-catenin is phosphorylated by GSK-3 as part of a tripartite axin protein complex resulting in β-catenin degradation (Ikeda, et al., *EMBO J.*, 1998, 17, 1371-1384). Inhibition of GSK-3 activity is involved in the stabilization of catenin hence promotes β-catenin-LEF-1/TCF transcriptional activity (Eastman, Grosschedl, *Curr. Opin. Cell Biol.*, 1999, 11, 233). Studies have also suggested that GSK-3 inhibitors may also be of value in treatment of schizophrenia (Cotter D., et al. *Neuroreport*, 1998, 9, 1379-1383; Lijam N., et al., *Cell*, 1997, 90, 895-905) and manic depression (Manji, et al., *J. Clin. Psychiatry*, 1999, 60, (Suppl 2) 27-39 for review).

Accordingly, compounds found useful as GSK-3 inhibitors could have further therapeutic utility in the treatment of diabetes, dermatological disorders, inflammatory diseases and central nervous system disorders.

Embodiments of the method of the present invention include a method for treating or ameliorating a kinase or dual-kinase mediated disorder in a subject in need thereof comprising administering to the subject a therapeutically effective amount of an instant compound or pharmaceutical composition thereof. The therapeutically effective amount of the compounds of Formula (I) exemplified in such a method is from about 0.001 mg/kg/day to about 300 mg/kg/day.

Embodiments of the present invention include the use of a compound of Formula (I) for the preparation of a medicament for treating or ameliorating a kinase or dual-kinase mediated disorder in a subject in need thereof.

In accordance with the methods of the present invention, an individual compound of the present invention or a pharmaceutical composition thereof can be administered separately at different times during the course of therapy or concurrently in divided or single combination forms. The instant invention is therefore to be understood as embracing all such regimes of simultaneous or alternating treatment and the term "administering" is to be interpreted accordingly.

Embodiments of the present method include a compound or pharmaceutical composition thereof advantageously co-administered in combination with other agents for treating or ameliorating a kinase or dual-kinase mediated disorder. For example, in the treatment of diabetes, especially Type II diabetes, a compound of Formula (I) or pharmaceutical composition thereof may be used in combination with other agents, especially insulin or antidiabetic agents including, but not limited to, insulin secretagogues (such as sulphonylureas), insulin sensitizers including, but not limited to, glitazone insulin sensitizers (such as thiazolidinediones) or biguanides or α glucosidase inhibitors.

The combination product comprises co-administration of a compound of Formula (I) or pharmaceutical composition thereof and an additional agent for treating or ameliorating a kinase or dual-kinase mediated disorder, the sequential administration of a compound of Formula (I) or pharmaceutical composition thereof and an additional agent for treating or ameliorating a kinase or dual-kinase mediated disorder, administration of a pharmaceutical composition containing a compound of Formula (I) or pharmaceutical composition thereof and an additional agent for treating or ameliorating a kinase or dual-kinase mediated disorder or the essentially simultaneous administration of a separate pharmaceutical composition containing a compound of Formula (I) or pharmaceutical composition thereof and a separate pharmaceutical composition containing an additional agent for treating or ameliorating a kinase or dual-kinase mediated disorder.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human, that is being sought by a researcher, veterinarian, medical doctor, or other clinician, which includes alleviation of the symptoms of the disease or disorder being treated.

The ubiquitous nature of the PKC and GSK isoforms and their important roles in physiology provide incentive to produce highly selective PKC and GSK inhibitors. Given the evidence demonstrating linkage of certain isoforms to disease states, it is reasonable to assume that inhibitory compounds that are selective to one or two PKC isoforms or to a GSK isoform relative to the other PKC and GSK isoforms and other protein kinases are superior therapeutic agents. Such compounds should demonstrate greater efficacy and lower toxicity by virtue of their specificity. Accordingly, it will be appreciated by one skilled in the art that a compound of Formula (I) is therapeutically effective for certain kinase or dual-kinase mediated disorders based on the modulation of the disorder by selective kinase or dual-kinase inhibition. The usefulness of a compound of Formula (I) as a selective kinase or dual-kinase inhibitor can be determined according to the methods disclosed herein and the scope of such use includes use in one or more kinase or dual-kinase mediated disorders.

Therefore, the term "kinase or dual-kinase mediated disorders" as used herein, includes, and is not limited to, cardiovascular diseases, diabetes, diabetes-associated disorders, inflammatory diseases, immunological disorders, dermatological disorders, oncological disorders and CNS disorders.

Cardiovascular diseases include, and are not limited to, acute stroke, heart failure, cardiovascular ischemia, thrombosis, atherosclerosis, hypertension, restenosis, retinopathy of prematurity or age-related macular degeneration. Diabetes includes insulin dependent diabetes or Type II non-insulin dependent diabetes mellitus. Diabetes-associated disorders include, and are not limited to, impaired glucose tolerance, diabetic retinopathy, proliferative retinopathy, retinal vein occlusion, macular edema, cardiomyopathy, nephropathy or neuropathy. Inflammatory diseases include, and are not limited to, vascular permeability, inflammation, asthma, rheumatoid arthritis or osteoarthritis. Immunological disorders include, and are not limited to; transplant tissue rejection, HIV-1 or immunological disorders treated or ameliorated by PKC modulation. Dermatological disorders include, and are not limited to, psoriasis, hair loss or baldness. Oncological disorders include, and are not limited to, cancers or tumor growth (such as breast, brain, kidney, bladder, ovarian or colon cancer or leukemia), proliferative angiopathy and angiogenesis; and, includes use for compounds of Formula (I) as an adjunct to chemotherapy and radiation therapy. CNS disorders include, and are not limited to, chronic pain, neuropathic pain, epilepsy, chronic neurodegenerative conditions (such as dementia or Alzheimer's disease), mood disorders (such as schizophrenia), manic depression or neurotraumatic, cognitive decline and ischemia-related diseases {as a result of head trauma (from acute ischemic stroke, injury or surgery) or transient ischemic stroke (from coronary bypass surgery or other transient ischemic conditions)}.

A compound may be administered to a subject in need of treatment by any conventional route of administration including, but not limited to oral, nasal, sublingual, ocular, transdermal, rectal, vaginal and parenteral (i.e. subcutaneous, intramuscular, intradermal, intravenous etc.).

To prepare the pharmaceutical compositions of this invention, one or more compounds of Formula (I) or salt thereof as the active ingredient, is intimately admixed with a pharmaceutical carrier according to conventional pharmaceutical compounding techniques, which carrier may take a wide variety of forms depending on the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients,* published by the American Pharmaceutical Association and the Pharmaceutical Society of Great Britain.

Methods of formulating pharmaceutical compositions have been described in numerous publications such as *Pharmaceutical Dosage Forms: Tablets,* Second Edition, Revised and Expanded, Volumes 1-3, edited by Lieberman, et al.; *Pharmaceutical Dosage Forms: Parenteral Medications,* Volumes 1-2, edited by Avis, et al.; and *Pharmaceutical Dosage Forms: Disperse Systems,* Volumes 1-2, edited by Lieberman, et al.; published by Marcel Dekker, Inc.

In preparing a pharmaceutical composition of the present invention in liquid dosage form for oral, topical and parenteral administration, any of the usual pharmaceutical media or excipients may be employed. Thus, for liquid dosage forms, such as suspensions (i.e. colloids, emulsions and dispersions) and solutions, suitable carriers and additives include but are not limited to pharmaceutically acceptable wetting agents, dispersants, flocculation agents, thickeners, pH control agents (i.e. buffers), osmotic agents, coloring agents, flavors, fragrances, preservatives (i.e. to control microbial growth, etc.) and a liquid vehicle may be employed. Not all of the components listed above will be required for each liquid dosage form.

In solid oral preparations such as, for example, powders, granules, capsules, caplets, gelcaps, pills and tablets (each including immediate release, timed release and sustained release formulations), suitable carriers and additives include but are not limited to diluents, granulating agents, lubricants, binders, glidants, disintegrating agents and the like. Because of their ease of administration, tablets and capsules represent the most advantageous oral dosage unit form, in which case solid pharmaceutical carriers are obviously employed. If desired, tablets may be sugar coated, gelatin coated, film coated or enteric coated by standard techniques.

The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.01 mg to about 300 mg (preferably, from about 0.1 mg to about 100 mg; and, more preferably, from about 0.1 mg to about 30 mg) and may be given at a dosage of from about 0.01 mg/kg/day to about 300 mg/kg/day (preferably, from about 0.1 mg/kg/day to about 100 mg/kg/day; and, more preferably, from about 0.1 mg/kg/day to about 30 mg/kg/day). Preferably, in the method for the treatment of kinase mediated disorders described in the present invention and using any of the compounds as defined herein, the dosage form will contain a pharmaceutically acceptable carrier containing between about 0.01 mg and 100 mg; and, more preferably, between about 5 mg and 50 mg of the compound; and, may be constituted into any form suitable for the mode of administration selected. The dosages, however, may be varied depending upon the requirement of the subjects, the severity of the condition being treated and the compound being employed. The use of either daily administration or post-periodic dosing may be employed.

Preferably these compositions are in unit dosage forms such as tablets, pills, capsules, powders, granules, lozenges, sterile parenteral solutions or suspensions, metered aerosol or liquid sprays, drops, ampoules, autoinjector devices or suppositories for administration by oral, intranasal, sublingual, intraocular, transdermal, parenteral, rectal, vaginal, inhalation or insufflation means. Alternatively, the composition may be presented in a form suitable for once-weekly or once-monthly administration; for example, an insoluble salt of the active compound, such as the decanoate salt, may be adapted to provide a depot preparation for intramuscular injection.

For preparing solid pharmaceutical compositions such as tablets, the principal active ingredient is mixed with a pharmaceutical carrier, e.g. conventional tableting ingredients such as diluents, binders, adhesives, disintegrants, lubricants, antiadherents and glidants. Suitable diluents include, but are not limited to, starch (i.e. corn, wheat, or potato starch, which may be hydrolized), lactose (granulated, spray dried or anhydrous), sucrose, sucrose-based diluents (confectioner's sugar; sucrose plus about 7 to 10 weight percent invert sugar; sucrose plus about 3 weight percent modified dextrins; sucrose plus invert sugar, about 4 weight percent invert sugar, about 0.1 to 0.2 weight percent cornstarch and magnesium stearate), dextrose, inositol, mannitol, sorbitol, microcrystalline cellulose (i.e. AVICEL™ microcrystalline cellulose available from FMC Corp.), dicalcium phosphate, calcium sulfate dihydrate, calcium lactate trihydrate and the like. Suitable binders and adhesives include, but are not limited to acacia gum, guar gum, tragacanth gum, sucrose, gelatin, glucose, starch, and cellulosics (i.e. methylcellulose, sodium carboxymethylcellulose, ethylcellulose, hydroxypropylmethylcellulose, hydroxypropylcellulose, and the like), water soluble or dispersible binders (i.e. alginic acid and salts thereof, magnesium aluminum silicate, hydroxyethylcellulose [i.e. TYLOSE™ available from Hoechst Celanese], polyethylene glycol, polysaccharide acids, bentonites, polyvinylpyrrolidone, polymethacrylates and pregelatinized starch) and the like. Suitable disintegrants include, but are not limited to, starches (corn, potato, etc.), sodium starch glycolates, pregelatinized starches, clays (magnesium aluminum silicate), celluloses (such as crosslinked sodium carboxymethylcellulose and microcrystalline cellulose), alginates, pregelatinized starches (i.e. corn starch, etc.), gums (i.e. agar, guar, locust bean, karaya, pectin, and tragacanth gum), crosslinked polyvinylpyrrolidone and the like. Suitable lubricants and antiadherents include, but are not limited to, stearates (magnesium, calcium and sodium), stearic acid, talc waxes, stearowet, boric acid, sodium chloride, DL-leucine, carbowax 4000, carbowax 6000, sodium oleate, sodium benzoate, sodium acetate, sodium lauryl sulfate, magnesium lauryl sulfate and the like. Suitable glidants include, but are not limited to, talc, cornstarch, silica (i.e. CAB-O-SIL™ silica available from Cabot, SYLOID™ silica available from W.R. Grace/Davison, and AEROSIL™ silica available from Degussa) and the like. Sweeteners and flavorants may be added to chewable solid dosage forms to improve the palatability of the oral dosage form. Additionally, colorants and coatings may be added or applied to the solid dosage form for ease of identification of the drug or for aesthetic purposes. These carriers are formulated with the pharmaceutical active to provide an accurate, appropriate dose of the pharmaceutical active with a therapeutic release profile.

Generally these carriers are mixed with the pharmaceutical active to form a solid preformulation composition containing a homogeneous mixture of the pharmaceutical active of the present invention, or a pharmaceutically acceptable salt thereof. Generally the preformulation will be formed by one of three common methods: (a) wet granulation, (b) dry granulation and (c) dry blending. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 0.1 mg to about 500 mg of the active ingredient of the present invention. The tablets or pills containing the novel compositions may also be formulated in multilayer tablets or pills to provide a sustained or provide dual-release products. For example, a dual release tablet or pill can comprise an inner dosage and an outer dosage component, the latter being in the form of an envelope over the former. The two components can be separated by an enteric layer, which serves to resist disintegration in the stomach and permits the inner component to pass intact into the duodenum or to be delayed in release. A variety of materials can be used for such enteric layers or coatings, such materials including a number of polymeric materials such as shellac, cellulose acetate (i.e. cellulose acetate phthalate), polyvinyl acetate phthalate, hydroxypropyl methylcellulose phthalate, hydroxypropyl methylcellulose acetate succinate, methacrylate and ethylacrylate copolymers, methacrylate and methyl methacrylate copolymers and the like. Sustained release tablets may also be made by film coating or wet granulation using slightly soluble or insoluble substances in solution (which for a wet granulation acts as the binding agents) or low melting solids a molten form (which in a wet granulation may incorporate the active ingredient). These materials include natural and synthetic polymers waxes, hydrogenated oils, fatty acids and alcohols (i.e. beeswax, carnauba wax, cetyl alcohol, cetylstearyl alcohol, and the like), esters of fatty acids metallic soaps, and other acceptable materials that can be used to granulate, coat, entrap or otherwise limit the solubility of an active ingredient to achieve a prolonged or sustained release product.

The liquid forms in which the novel compositions of the present invention may be incorporated for administration orally or by injection include, but are not limited to aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable suspending agents for aqueous suspensions, include synthetic and natural gums such as, acacia, agar, alginate (i.e. propylene alginate, sodium alginate and the like), guar, karaya, locust bean, pectin, tragacanth, and xanthan gum, cellulosics such as sodium carboxymethylcellulose, methylcellulose, hydroxymethylcellulose, hydroxyethylcellulose, hydroxypropylcellulose and hydroxypropyl methylcellulose, and combinations thereof, synthetic polymers such as polyvinyl pyrrolidone, carbomer (i.e. carboxypolymethylene), and polyethylene glycol; clays such as bentonite, hectorite, attapulgite or sepiolite; and other pharmaceutically acceptable suspending agents such as lecithin, gelatin or the like. Suitable surfactants include but are not limited to sodium docusate, sodium lauryl sulfate, polysorbate, octoxynol-9, nonoxynol-10, polysorbate 20, polysorbate 40, polysorbate 60, polysorbate 80, polyoxamer 188, polyoxamer 235 and combinations thereof. Suitable deflocculating or dispersing agent include pharmaceutical grade lecithins. Suitable flocculating agent include but are not limited to simple neutral electrolytes (i.e. sodium chloride, potassium, chloride, and the like), highly charged insoluble polymers and polyelectrolyte species, water soluble divalent or trivalent ions (i.e. calcium salts, alums or sulfates, citrates and phosphates (which can be used jointly in formulations as pH buffers and flocculating agents). Suitable preservatives include but are not limited to parabens (i.e. methyl, ethyl, n-propyl and n-butyl), sorbic acid, thimerosal, quaternary ammonium salts, benzyl alcohol, benzoic acid, chlorhexidine gluconate, phenylethanol and the like.

There are many liquid vehicles that may be used in liquid pharmaceutical dosage forms, however, the liquid vehicle that is used in a particular dosage form must be compatible with the suspending agent(s). For example, nonpolar liquid vehicles such as fatty esters and oils liquid vehicles are best used with suspending agents such as low HLB (Hydrophile-Lipophile Balance) surfactants, stearalkonium hectorite, water insoluble resins, water insoluble film forming polymers and the like. Conversely, polar liquids such as water, alcohols, polyols and glycols are best used with suspending agents such as higher HLB surfactants, clays silicates, gums, water soluble cellulosics, water soluble polymers and the like. For parenteral administration, sterile suspensions and solutions are desired. Liquid forms useful for parenteral administration include sterile solutions, emulsions and suspensions. Isotonic preparations which generally contain suitable preservatives are employed when intravenous administration is desired.

Furthermore, compounds of the present invention can be administered in an intranasal dosage form via topical use of suitable intranasal vehicles or via transdermal skin patches, the composition of which are well known to those of ordinary skill in that art. To be administered in the form of a transdermal delivery system, the administration of a therapeutic dose will, of course, be continuous rather than intermittent throughout the dosage regimen.

Compounds of the present invention can also be administered in the form of liposome delivery systems, such as small unilamellar vesicles, large unilamellar vesicles, multilamellar vesicles and the like. Liposomes can be formed from a variety of phospholipids, such as cholesterol, stearylamine, phosphatidylcholines and the like.

Compounds of the present invention may also be delivered by the use of monoclonal antibodies as individual carriers to which the compound molecules are coupled. The compounds of the present invention may also be coupled with soluble polymers as targetable drug carriers. Such polymers can include, but are not limited to polyvinylpyrrolidone, pyran copolymer, polyhydroxypropylmethacrylamidephenol, polyhydroxy-ethylaspartamidephenol, or polyethyl eneoxidepolylysine substituted with palmitoyl residue. Furthermore, the compounds of the present invention may be coupled to a class of biodegradable polymers useful in achieving controlled release of a drug, for example, to homopolymers and copolymers (which means polymers containing two or more chemically distinguishable repeating units) of lactide (which includes lactic acid d-, l- and meso lactide), glycolide (including glycolic acid), ε-caprolactone, p-dioxanone (1,4-dioxan-2-one), trimethylene carbonate (1,3-dioxan-2-one), alkyl derivatives of trimethylene carbonate, δ-valerolactone, β-butyrolactone, γ-butyrolactone, ε-decalactone, hydroxybutyrate, hydroxyvalerate, 1,4-dioxepan-2-one (including its dimer 1,5,8,12-tetraoxacyclotetradecane-7,14-dione), 1,5-dioxepan-2-one, 6,6-dimethyl-1,4-dioxan-2-one, polyorthoesters, polyacetals, polydihydropyrans, polycyanoacrylates and cross-linked or amphipathic block copolymers of hydrogels and blends thereof.

Compounds of this invention may be administered in any of the foregoing compositions and dosage regimens or by means of those compositions and dosage regimens established in the art whenever treatment of kinase mediated disorders, particularly protein kinase or glycogen synthase kinase mediated disorders, is required for a subject in need thereof.

The daily dose of a pharmaceutical composition of the present invention may be varied over a wide range from about 0.7 mg to about 21,000 mg per 70 kilogram (kg) adult human per day; preferably in the range of from about 7 mg to about 7,000 mg per adult human per day; and, more preferably, in the range of from about 7 mg to about 2,100 mg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the subject to be treated. A therapeutically effective amount of the drug is ordinarily supplied at a dosage level of from about 0.01 mg/kg to about 300 mg/kg of body weight per day. Preferably, the range is from about 0.1 mg/kg to about 100 mg/kg of body weight per day; and, most preferably, from about 0.1 mg/kg to about 30 mg/kg of body weight per day. Advantageously, compounds of the present invention may be administered in a single daily dose or the total daily dosage may be administered in divided doses of two, three or four times daily.

Optimal dosages to be administered may be readily determined by those skilled in the art, and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level.

Abbreviations used in the instant specification, particularly the Schemes and Examples, are as follows:

| | |
|---|---|
| ATP = | adenosinetriphosphate |
| BSA = | bovine serum albumin |
| DCM = | dichloromethane |
| DMF = | N,N-dimethylformamide |
| DMSO = | dimethylsulfoxide |
| EDTA = | ethylenediaminetetraacetic acid |
| EGTA = | ethylenebis(oxyethylenenitrilo)tetraacetic acid |
| h = | hour |
| HEPES = | 4-(2-hydroxyethyl)-1-piperazine-ethanesulfonic acid |
| min = | minute |
| NT = | not tested |
| rt = | room temperature |
| TBAF = | tert-butylammonium fluoride |
| TCA = | trichloroacetic acid |
| THF = | tetrahydrofuran |
| TFA = | trifluoroacetic acid |
| SEM = | 2-(trimethylsilyl)ethoxymethyl |

General Synthetic Methods

Representative compounds of the present invention can be synthesized in accordance with the general synthetic methods described below and are illustrated more particularly in the schemes that follow. Since the schemes are an illustration, the invention should not be construed as being limited by the chemical reactions and conditions expressed. The preparation of the various starting materials used in the schemes is well within the skill of persons versed in the art.

The following schemes describe general synthetic methods whereby intermediate and target compounds of the present invention may be prepared. Additional representative compounds of the present invention can be synthesized using the intermediates prepared in accordance with the schemes and other materials, compounds and reagents known to those skilled in the art.

In Scheme AA, the 4-aminopyridine 5-azaindole AA1 (optionally substituted with $R^3$) was treated with iodine monochloride in HOAc to give AA2 which was coupled with (trimethylsilyl)acetylene in the presence of a palladium catalyst, such as $Pd(PPh_3)_2Cl_2$, and CuI to afford AA3. Compound AA3 was treated with (Boc)$_2$O in the presence of a base such as NaH to provide AA4 which was then cyclized in the presence of CuI followed by removal of Boc group with an acid such as TFA to afford 5-azaindole AA5.

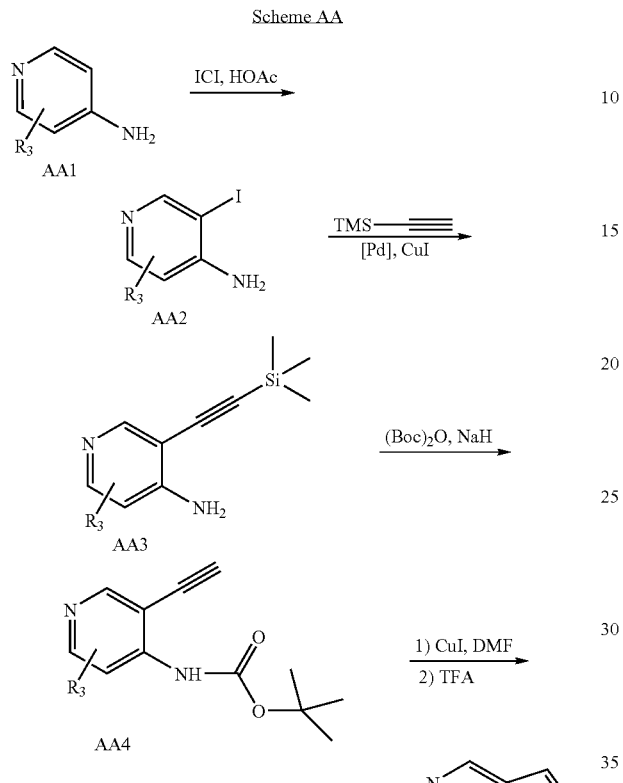

In Scheme AB, 5-azaindole AA5 was treated ethylmagnesium bromide followed by acylation with methylchlorooxoacetate to give Compound AB1. Compound AB1 was then alkylated with an appropriate alkylating agent in the presence of a base such as cesium or potassium carbonate in a dipolar aprotic solvent such as DMF to give Compound AB2 (wherein $R^1$ was a substituted or unsubstituted alkyl group).

Alternatively, Compound AA5 was treated with an appropriate alkylating agent under basic conditions (wherein $R^1$ was a substituted or unsubstituted alkyl group), or an appropriate aryl or heteroaryl halide in the presence of a base such as cesium or potassium carbonate and copper oxide in a dipolar aprotic solvent such as DMF (wherein $R^1$ was a substituted or unsubstituted aryl or heteroaryl group) to give Compound AB3. Acylation of AB3 with oxalyl chloride in an aprotic solvent such as diethyl ether or DCM followed by addition of methanol or sodium methoxide afforded Compound AB2.

The glyoxylate ester Compound AB2 was then reacted with an acetamide Compound AB4 (substituted with R(R$_2$, R$_4$); wherein the "R" group is selected from cycloalkyl, heterocyclyl, aryl and heteroaryl; and, is preferably selected from an aromatic, heteroaromatic or partially saturated heterocyclic ring system) stirred in an aprotic solvent such as THF with ice bath cooling and a base, such as potassium tert-butoxide or sodium hydride, to give a target Compound AB5.

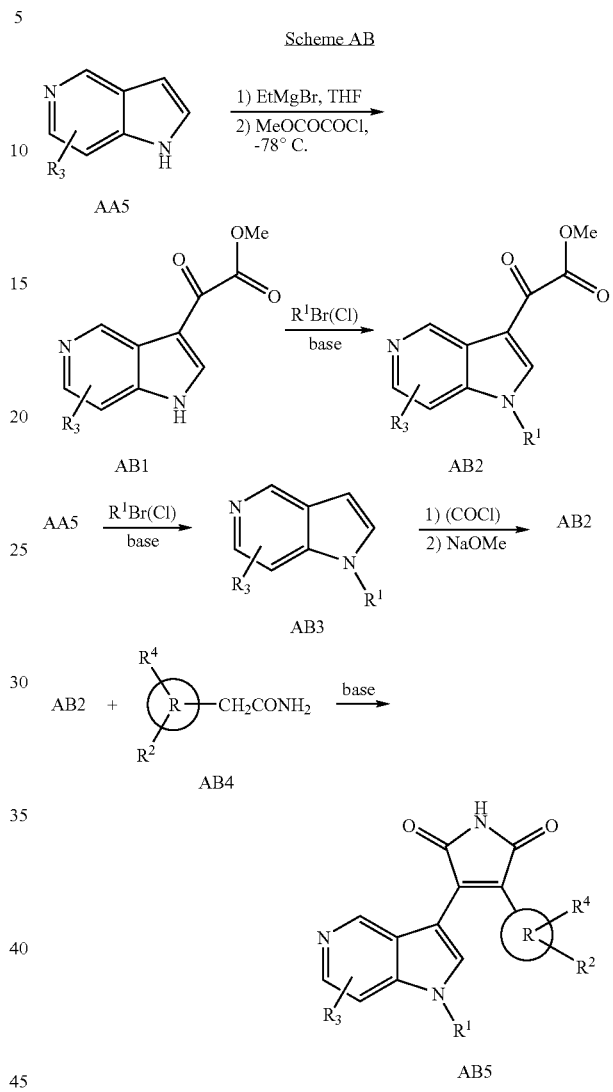

Specific Synthetic Methods

Specific compounds which are representative of this invention were prepared as per the following examples and reaction sequences; the examples and the diagrams depicting the reaction sequences are offered by way of illustration, to aid in the understanding of the invention and should not be construed to limit in any way the invention set forth in the claims which follow thereafter. The depicted intermediates may also be used in subsequent examples to produce additional compounds of the present invention. No attempt has been made to optimize the yields obtained in any of the reactions. One skilled in the art would know how to increase such yields through routine variations in reaction times, temperatures, solvents and/or reagents.

All chemicals were obtained from commercial suppliers and used without further purification. $^1$H and $^{13}$C NMR spectra were recorded on a Bruker AC 300B (300 MHz proton) or a Bruker AM-400 (400 MHz proton) spectrometer with Me$_4$Si as an internal standard (s=singlet, d=doublet, t=triplet, br=broad). APCI-MS and ES-MS were recorded on a VG Platform II mass spectrometer; methane was used for chemical ionization, unless noted otherwise. Accurate mass measurements were obtained by using a VG ZAB 2-SE spectrometer in the FAB mode. TLC was performed with Whatman 250-μm silica gel plates. Preparative TLC was performed with Analtech 1000-μm silica gel GF plates. Flash column chromatography was conducted with flash column silica gel (40-63 μm) and column chromatography was conducted with standard silica gel. HPLC separations were carried out on three Waters PrepPak® Cartridges (25×100 mm, Bondapak® C18, 15-20 μm, 125 Å) connected in series; detection was at 254 nm on a Waters 486 UV detector. Analytical HPLC was carried out on a Supelcosil ABZ+PLUS column (5 cm×2.1 mm), with detection at 254 nm on a Hewlett Packard 1100 UV detector. Microanalysis was performed by Robertson Microlit Laboratories, Inc.

Compounds are named according to nomenclature conventions well known in the art or, as in the compound names for the examples presented, may be generated using commercial chemical naming software such as the ACD/Index Name (Advanced Chemistry Development, Inc., Toronto, Ontario).

EXAMPLE 1

3-(2-Methoxyphenyl)-4-[1-(3-methoxypropyl)-1H-pyrrolo[3,2-c]pyridin-3-yl]-1H-pyrrole-2,5-dione (Compound 1)

To a solution of 4-aminopyridine (1a, 37.65 g, 0.4 mole) in HOAc (200 mL) was added iodine monchloride (130 g, 0.8 mole) portionwise. The reaction mixture was stirred at 45° C. for 20 h, then diluted with water (500 mL). The mixture was cooled to 0° C., and basified 30% NaOH to pH=9-10. The solution was extracted with EtOAc (1 L×2) and the combined extracts were washed with 15% $Na_2S_2O_3$ (400 mL×2), water, brine, dried over $Na_2SO_4$, and evaporated in vacuo to give 1b (62 g) as a light yellow solid. ES-MS m/z 221 (MH$^+$).

Into a pressure flask was added 1b (4.4 g, 20 mmol), cupric iodide (228 mg, 1.2 mmol), (trimethylsilyl)acetylene (7.08 g, 72 mmol), triethylamine (200 mL) and DMF (80 mL). The mixture was stirred under nitrogen for 10 min, followed by addition of Pd(PPh$_3$)$_2$Cl$_2$ (0.84 g, 1.2 mmol). The mixture was then stirred to 70° C. for 5 h, and then diluted with ethyl acetate (600 mL). The solution was washed with $H_2O$ (250 mL×2), brine (250 mL), dried over $Na_2SO_4$, and evaporated in vacuo to give crude product which was purified by flash chromatography (100% $CH_2Cl_2$ to 2% MeOH in $CH_2Cl_2$) to afford Compound 1c (2.97 g, 78%) as a light brown solid. $^1$H NMR (CDCl$_3$) δ 8.37 (s, 1H), 8.13 (d, J=5.7 Hz, 1H), 6.53 (d, J=5.6 Hz, 1H), 4.67 (bs, 2H), 0.27 (s, 9H). ES-MS m/z 191 (MH$^+$).

Into an ice-cold solution of 1c (1.35 g, 7.1 mmol) in THF (50 mL) was added 95% NaH (1.86 g, 8.5 mmol). The mixture was stirred at 0° C. for 10 min, rt for 10 min, then cooled back to 0° C. (Boc)$_2$O (1.86 g, 8.5 mmol) was added and the mixture was stirred at 0° C. for 30 min and then rt for 2 h. Additional 95% NaH (0.08 g, 3.5 mmol) and (Boc)$_2$O (0.2 g, 0.92 mmol) were added and the mixture was stirred at rt for another 2 h. The reaction was then quenched slowly with saturated NaHCO$_3$ (10 mL), extracted with ethyl acetate (200 mL×2). The organic layer was washed with brine, dried over $Na_2SO_4$, and evaporated in vacuo. The crude product was purified by flash chromatography (EtOAc/hexane; 1:3) to give 1d (0.67 g). ES-MS m/z 219 (MH$^+$).

To a solution of 1d (1.3 g, 4.5 mmol) in DMF (20 mL) was added cupric iodide (0.85 g, 4.5 mmol). The mixture was stirred at 80° C. for 6 h and then filtered. The filtrate was extracted with ethyl acetate (100 mL×3), and the organic layer was washed with $H_2O$, brine, dried ($Na_2SO_4$) and concentrated. The residue was purified by flash chromatography (Ethyl acetate/hexane; 1:3) to give Compound 1e (0.25 g, 26%). $^1$H NMR (CDCl$_3$) δ 8.89 (s, 1H), 8.47 (d, J=5.8 Hz, 1H), 7.98 (d, J=5.7 Hz, 1H), 7.62 (d, J=3.7 Hz, 1H), 6.66 (d, J=3.7 Hz, 1H), 1.69 (s, 9H). ES-MS m/z 219 (MH$^+$).

To a solution of 1e (0.178 g, 0.82 mmol) in methylene chloride (5 mL) was added TFA (1.0 mL) slowly. The mixture was stirred at rt for 1.5 h, and The solvent was evaporated to obtain 5-azaindole 1f as a white solid (0.18 g, 95%). $^1$H NMR (CDCl$_3$) δ 8.97 (s, 1H), 8.31 (d, J=5.7 Hz, 1H), 7.35 (d, J=5.7 Hz, 1H), 7.29 (m, 1H), 6.68 (d, J=3.3 Hz, 1H). ES-MS m/z 119 (MH$^+$).

A mixture of Compound 1f (0.26 g, 2.2 mmol) and cesium carbonate (1.43 g, 4.4 mmol) in DMF (10 mL) was stirred at rt for 10 min, and then 3-methoxypropylbromide (0.40 g, 2.64 mmol) was added. The reaction mixture was stirred at 60° C. for 3 h. The solvent was evaporated and the residue was partitioned between EtOAc (150 mL) and water (100 mL). The organic layer was washed with water (3×50 mL), brine (2×50 mL), then dried ($Na_2SO_4$) and evaporated in vacuo to give a brown oil. The crude product was purified by flash column chromatography (from 100% DCM to DCM/MeOH/NH$_4$OH; 97:3:0.3) to afford Compound 1g (0.26 g, 62%) as light brown oil. $^1$H NMR (CDCl$_3$) δ 8.91 (s, 1H), 8.31 (d, J=5.8 Hz, 1H), 7.27 (s, 1H), 7.11 (d, J=3.2 Hz, 1H), 6.60 (d, J=3.3 Hz, 1H), 4.25 (t, J=6.7 Hz, 2H), 3.32 (s, 3H), 3.25 (t, J=5.7 Hz, 2H), 2.05 (m, 2H). ES-MS m/z 191(MH$^+$).

Oxalyl chloride (3 mL) was added slowly to a solution of compound 1g (0.22 g, 1.14 mmol) in ether (5 mL). The mixture was heated to 48° C. in a pressure tube overnight. TLC shown that some starting materials were still present. Additional 0.5 mL of oxalyl chloride was added and stirring was continuted at 48° C. for another night. The mixture was then cooled down to rt, to which methanol (3 mL) was added. The mixture was heated to 48° C. and stirred for 2 h. The volatiles removed under vacuo and the residue was purified by flash chromatography (from 100% DCM to DCM/MeOH/NH$_4$OH; 97:3:0.3) to afford Compound 1h (0.15 g, 48%) as a white solid. $^1$H NMR (CDCl$_3$) δ 8.51 (d, J=5.8 Hz, 1H), 8.44 (s, 1H), 7.37 (m, 1H), 4.34 (t, J=6.8 Hz, 2H), 3.97 (s, 3H), 3.35 (s, 3H), 3.30 (t, J=5.7 Hz, 2H), 2.12 (m, 2H). ES-MS m/z 277 (MH$^+$).

The α-ketoester Compound 1h (53.8 mg, 0.20 mmol) and amide Compound 1i (23 mg, 0.14 mmol) were combined in dry THF (3 mL) under argon and cooled with an ice bath as a solution of 1.0 M potassium t-butoxide in THF (1 mL, 1 mmol) was added dropwise. The mixture was stirred at 0° C. for 30 min, then rt for 2 h. The reaction mixture was cooled in an ice bath, and 12 N HCl (4 mL) was added slowly. The mixture was stirred for 20 min and then basified with 3 N NaOH, followed by EtOAc extraction. The organic extracts were combined, washed with brine, dried ($Na_2SO_4$) and evaporated in vacuo to a yellow oil, which was purified by flash column chromatography (from 100% DCM to (DCM/MeOH/NH$_4$OH; 93:7:0.7) to afford Compound 1 (25 mg, 32%) as an orange-yellow flaky solid. $^1$H NMR (CDCl$_3$) δ 8.25 (d, J=5.8 Hz, 1H), 8.01 (s, 1H), 7.65 (s, 1H), 7.44 (t, J=8.7 Hz, 1H), 7.39 (d, J=7.6 Hz, 1H), 7.24 (m, 1H), 7.03 (t, J=7.5 Hz, 1H), 6.89 (d, J=8.4 Hz, 1H), 4.32 (t, J=6.7 Hz, 2H), 3.38 (s, 3H), 3.35 (s, 3H), 3.29 (t, J=5.6 Hz, 2H), 2.10 (m, 2H). ES-MS m/z 392 (MH$^+$). HRMS (FAB) Calcd for $C_{22}H_{21}N_3O_4$+H$^+$, 392.1629; Found, 392.1610.

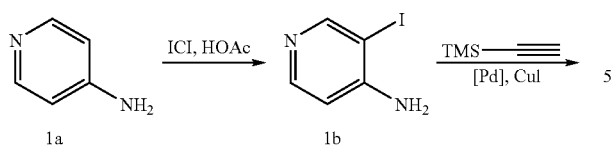

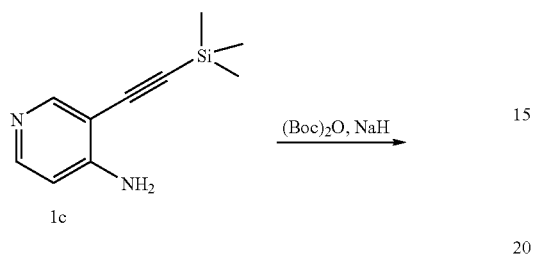

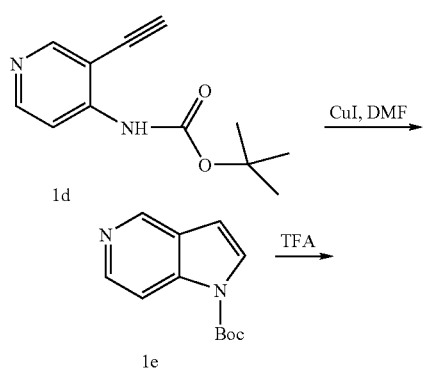

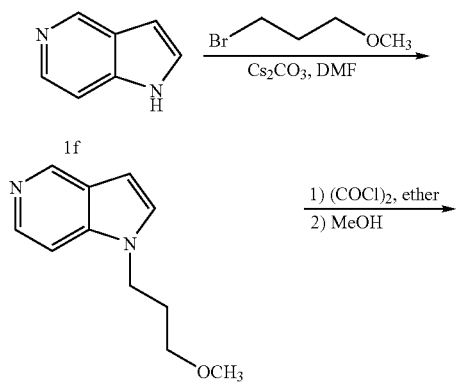

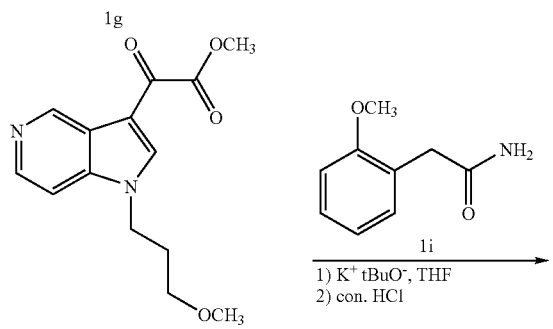

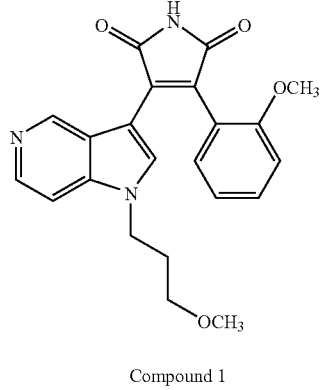

Compound 1

EXAMPLE 2

3-(2-Chlorophenyl)-4-[1-(3-methoxypropyl)-1H-pyrrolo[3,2-c]pyridin-3-yl]-1H-pyrrole-2,5-dione (Compound 2)

The α-ketoester Compound 1h (44 mg, 0.16 mmol) and amide Compound 2a (19.3 mg, 0.11 mmol) were combined in dry THF (4 mL) under argon and cooled with an ice bath as a solution of 1.0 M potassium t-butoxide in THF (0.7 mL, 0.7 mmol) was added dropwise. The mixture was stirred at 0° C. with for 30 min, then rt for 2 h. The reaction solution was cooled back to 0° C., and quenched with 12 N HCl (4 mL). The mixture was stirred for 20 min and then basified with 3 N NaOH. The mixture was extracted with EtOAc and the combined extracts were washed with brine, dried ($Na_2SO_4$) and evaporated in vacuo to a yellow oil, which was then purified by flash column chromatography (DCM/MeOH/$NH_4OH$; 93:7:0.7) to afford Compound 2 (6 mg) as an orange-yellow flaky solid. $^1$H NMR ($CDCl_3$) δ 8.27 (d, J=5.7 Hz, 1H), 8.08 (s, 1H), 7.59 (s, 1H), 7.39 (m, 4H), 7.28 (m, 1 H), 4.32 (t, J=6.7 Hz, 2H), 3.34 (s, 3H), 3.27 (t, J=5.6 Hz, 2H), 2.10 (m, 2H). ES-MS m/z 396 ($MH^+$).

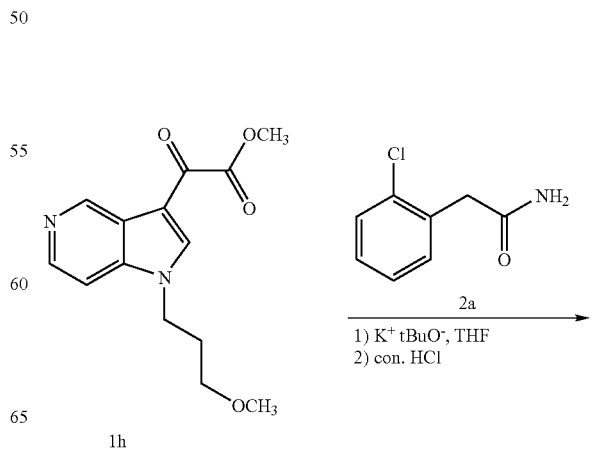

-continued

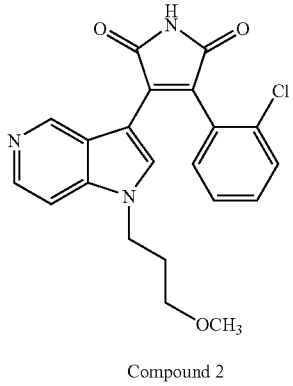

Compound 2

Biological Experimental Examples

The utility of the compounds to treat kinase or dual-kinase mediated disorders (in particular, kinases selected from glycogen synthase kinase-3 and protein kinase C; and, more particularly, kinases selected from glycogen synthase kinase-3β, protein kinase C α, protein kinase C β-II, or protein kinase C γ) was determined using the following procedures.

Glycogen Synthase Kinase-3 Assay

Compounds were tested for the ability to inhibit recombinant rabbit GSK-3β protein using the following protocol. The test compound was added to a reaction mixture containing Protein Phosphatase Inhibitor-2 (PPI-2) (Calbiochem) (45 ng), rabbit GSK-3β protein (New England Biolabs) (0.75 units) and $^{33}$P-ATP (1 µCi) in 50 mM Tris-HCl (pH 8.0), 10 mM MgCl$_2$, 0.1% BSA, 1 mM DTT and 100 µM Sodium Vanadate. The mixture was reacted for 90 minutes at 30° C. to allow phosphorylation of the PPI-2 protein and then the protein in the reaction was precipitated using 10% TCA. The precipitated protein was collected on filter plates (Multi-Screen-DV/Millipore), which were subsequently washed. Finally, the radioactivity was quantified using a TopCount Scintillation Counter (Packard). GSK-3 inhibitory compounds resulted in less phosphorylated PPI-2 and thus a lower radioactive signal in the precipitated protein. Staurosporine or Valproate, known inhibitors of GSK-3β, were used as a positive control for screening.

Protein Kinase C Histone-Based Assay

Compounds were evaluated for PKC isozyme selectivity using histone III as the substrate. PKC isozymes α, β-II or γ were added to a reaction mixture that contained 20 mM HEPES, (pH 7.4), 940 µM CaCl$_2$, 10 mM MgCl$_2$, 1 mM EGTA. 100 µg/mL phosphatidylserine, 20 µg/mL diacylglycerol, 30 µM ATP, 1 pCi [$^{33}$P]ATP and 200 µg/mL histone III. The reaction was incubated for 10 min at 30° C. Reactions were terminated by TCA precipitation and spotting on Whatman P81 filters. Filters were washed in 75 mM phosphoric acid and the radioactivity quantified by liquid scintillation counting.

Table 2 shows the biological activity in the GSK-3β and PKC (histone) assays as an IC$_{50}$ value (µM) or in % inhibition for representative compounds of the present invention.

TABLE 2

| | Biological Activity (IC$_{50}$ µM, or % inhibition) | | | |
|---|---|---|---|---|
| Cpd | GSK-3β | PKC-α | PKC-βII | PKC-γ |
| 1 | 0.0018 µM | 31%@10 µM | 22%@1 µM | 25%@10 µM |
| 2 | 0.020 µM | 2.51 µM | 28%@1 µM | 4.21 µM |

The results from the foregoing indicate that a compound of the present invention would be expected to be useful in treating or ameliorating a kinase or dual-kinase mediated disorder.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A compound of Formula (I):

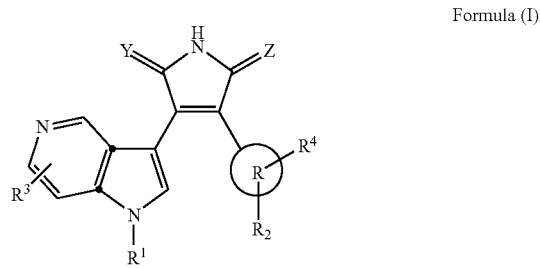

Formula (I)

wherein

R is selected from the group consisting of R$_a$, —C$_{1-8}$alkyl-R$_a$, —C$_{2-8}$alkenyl-R$_a$, —C$_{2-8}$alkynyl-R$_a$ and cyano;

R$_a$ is selected from the group consisting of dihydro-pyranyl, phenyl, naphthyl, thienyl, pyrrolyl, imidazolyl, pyrazolyl, pyridinyl, azaindolyl, indazolyl, benzofuryl, benzothienyl, dibenzofuryl and dibenzothienyl;

R$^1$ is selected from the group consisting of hydrogen, —C$_{1-8}$ alkyl-R$^5$, —C$_{2-8}$alkenyl-R$^5$, —C$_{2-8}$alkynyl-R$^5$, —C(O)—(C$_{1-8}$)alkyl-R$^9$, —C(O)-aryl-R$^8$, —C(O)—O—(C$_{1-8}$)alkyl-R$^9$, —C(O)—O-aryl-R$^8$, —C(O)—NH(C$_{1-8}$alkyl-R$^9$), —C(O)—NH(aryl-R$^8$), —C(O)—N(C$_{1-8}$alkyl-R$^9$)$_2$, —SO$_2$—(C$_{1-8}$)alkyl-R$^9$, —SO$_2$-aryl-R$^8$, -cycloalkyl-R$^6$, and aryl-R$^6$;

R$^5$ is 1 to 2 substituents independently selected from the group consisting of hydrogen, —O—(C$_{1-8}$)alkyl, —O—(C$_{1-8}$)alkyl-OH, —O—(C$_{1-8}$)alkyl-O—(C$_{1-8}$) alkyl, —O—(C$_{1-8}$)alkyl-NH$_2$, —O—(C$_{1-8}$)alkyl-NH(C$_{1-8}$alkyl), —O—(C$_{1-8}$)alkyl-N(C$_{1-8}$alkyl)$_2$, —O—(C$_{1-8}$)alkyl-S—(C$_{1-8}$)alkyl, —O—(C$_{1-8}$)alkyl-SO$_2$—(C$_{1-8}$)alkyl, —O—(C$_{1-8}$)alkyl-SO$_2$—NH$_2$, —O—(C$_{1-8}$) alkyl-SO$_2$—NH(C$_{1-8}$alkyl), —O—(C$_{1-8}$) alkyl-SO$_2$—N(C$_{1-8}$alkyl)$_2$, —O—C(O)H, —O—C(O)—(C$_{1-8}$) alkyl, —O—C(O)—NH$_2$, —O—C(O)—NH(C$_{1-8}$ alkyl), —O—C(O)—N(C$_{1-8}$alkyl)$_2$, —O—(C$_{1-8}$)alkyl-C(O)H, —O—(C$_{1-8}$)alkyl-C(O)—(C$_{1-8}$) alkyl, —O—(C$_{1-8}$)alkyl-CO$_2$H, —O—(C$_{1-8}$)alkyl-C(O)—O—(C$_{1-8}$) alkyl, —O—(C$_{1-8}$)alkyl-C(O)—NH$_2$, —O—(C$_{1-8}$)alkyl-C(O)—NH(C$_{1-8}$alkyl), —O—(C$_{1-8}$) alkyl-C(O)—N(C$_{1-8}$alkyl)$_2$, —C(O)H, —C(O)—(C$_{1-8}$) alkyl, —CO$_2$H, —C(O)—O—(C$_{1-8}$)alkyl, —C(O)—NH$_2$, —C(NH)—NH$_2$, —C(O)—NH(C$_{1-8}$alkyl), —C(O)—N(C$_{1-8}$alkyl)$_2$, —SH, —S—(C$_{1-8}$)alkyl, —S—(C$_{1-8}$)

alkyl-S—($C_{1-8}$)alkyl, —S—($C_{1-8}$)alkyl-O—($C_{1-8}$)alkyl, —S—($C_{1-8}$)alkyl-O—($C_{1-8}$)alkyl-OH, —S—($C_{1-8}$)alkyl-O—($C_{1-8}$)alkyl-$NH_2$, —S—($C_{1-8}$)alkyl-O—($C_{1-8}$)alkyl-NH($C_{1-8}$alkyl), —S—($C_{1-8}$)alkyl-O—($C_{1-8}$)alkyl-N($C_{1-8}$alkyl)$_2$, —S—($C_{1-8}$)alkyl-NH($C_{1-8}$ alkyl), —$SO_2$—($C_{1-8}$)alkyl, —$SO_2$—$NH_2$, —$SO_2$—NH($C_{1-8}$alkyl), —$SO_2$—N($C_{1-8}$alkyl)$_2$, —N—$R^7$, cyano, (halo)$_{1-3}$, hydroxy, nitro, oxo, -cycloalkyl-$R^6$, and -aryl-$R^6$;

$R^6$ is 1 to 4 substituents attached to a carbon or nitrogen atom independently selected from the group consisting of hydrogen, —$C_{1-8}$alkyl, —$C_{2-8}$alkenyl, —$C_{2-8}$alkynyl, —C(O)H, —C(O)—($C_{1-8}$)alkyl, —$CO_2$H, —C(O)—O—($C_{1-8}$)alkyl, —C(O)—$NH_2$, —C(NH)—$NH_2$, —C(O)—NH($C_{1-8}$alkyl), —C(O)—N($C_{1-8}$ alkyl)$_2$, —$SO_2$—($C_{1-8}$)alkyl, —$SO_2$—$NH_2$, —$SO_2$—NH($C_{1-8}$alkyl), —$SO_2$—N($C_{1-8}$alkyl)$_2$, —($C_{1-8}$)alkyl-N—$R^7$, —($C_{1-8}$)alkyl-(halo)$_{1-3}$, —($C_{1-8}$)alkyl-OH, -aryl-$R^8$, and —($C_{1-8}$)alkyl-aryl-$R^8$;

with the proviso that, when $R^6$ is attached to a carbon atom, $R^6$ is further selected from the group consisting of —$C_{1-8}$ alkoxy, —($C_{1-8}$)alkoxy-(halo)$_{1-3}$, —SH, —S—($C_{1-8}$)alkyl, —N—$R^7$, cyano, halo, hydroxy, nitro and oxo;

$R^7$ is 2 substituents independently selected from the group consisting of hydrogen, —$C_{1-8}$alkyl, —$C_{2-8}$alkenyl, —$C_{2-8}$alkynyl, —($C_{1-8}$)alkyl-OH, —($C_{1-8}$)alkyl-O—($C_{1-8}$)alkyl, —($C_{1-8}$)alkyl-$NH_2$, —($C_{1-8}$)alkyl-NH($C_{1-8}$ alkyl), —($C_{1-8}$)alkyl-N($C_{1-8}$alkyl)$_2$, —($C_{1-8}$)alkyl-S—($C_{1-8}$)alkyl, —C(O)H, —C(O)—($C_{1-8}$)alkyl, —C(O)—O—($C_{1-8}$)alkyl, —C(O)—$NH_2$, —C(O)—NH($C_{1-8}$ alkyl), —C(O)—N($C_{1-8}$alkyl)$_2$, —$SO_2$—($C_{1-8}$)alkyl, —$SO_2$—$NH_2$, —$SO_2$—NH($C_{1-8}$alkyl), —$SO_2$—N($C_{1-8}$ alkyl)$_2$, —C(N)—$NH_2$, -cycloalkyl-$R^8$, -aryl-$R^8$ and —($C_{1-8}$)alkyl-aryl-$R^8$;

$R^8$ is 1 to 4 substituents attached to a carbon or nitrogen atom independently selected from the group consisting of hydrogen, —$C_{1-8}$alkyl, —($C_{1-8}$)alkyl-(halo)$_{1-3}$ and —($C_{1-8}$)alkyl-OH;

with the proviso that, when $R^8$ is attached to a carbon atom, $R^8$ is further selected from the group consisting of —$C_{1-8}$alkoxy, —$NH_2$, —NH($C_{1-8}$alkyl), —N($C_{1-8}$alkyl)$_2$, cyano, halo, —($C_{1-8}$)alkoxy-(halo)$_{1-3}$, hydroxy and nitro;

$R^9$ is 1 to 2 substituents independently selected from the group consisting of hydrogen, —$C_{1-8}$alkoxy, —$NH_2$, —NH($C_{1-8}$alkyl), —N($C_{1-8}$alkyl)$_2$, cyano, (halo)$_{1-3}$, hydroxy and nitro;

$R^2$ is one substituent attached to a carbon or nitrogen atom selected from the group consisting of hydrogen, —$C_{1-8}$alkyl-$R^5$, —$C_{2-8}$alkenyl-$R^5$, —$C_{2-8}$alkynyl-$R^5$, —C(O)H, —C(O)—($C_{1-8}$)alkyl-$R^9$, —C(O)—$NH_2$, —C(O)—NH($C_{1-8}$alkyl-$R^9$), —C(O)—N ($C_{1-8}$alkyl-$R^9$)$_2$, —C(O)—NH(aryl-$R^8$), —C(O)-cycloalkyl-$R^8$, —C(O)-aryl-$R^8$, —$CO_2$H, —C(O)—O—($C_{1-8}$)alkyl-$R^9$, —C(O)-aryl-$R^8$, —$SO_2$—($C_{1-8}$)alkyl-$R^9$, —$SO_2$-aryl-$R^8$, -cycloalkyl-$R^6$, -aryl-$R^6$ and —($C_{1-8}$)alkyl-N—$R^7$;

with the proviso that, when $R^2$ is attached to a carbon atom, $R^2$ is further selected from the group consisting of —$C_{1-8}$ alkoxy-$R^5$, —N—$R^7$, cyano, halogen, hydroxy, nitro and oxo;

$R^3$ is 1 to 3 substituents attached to a carbon atom independently selected from the group consisting of hydrogen, —$C_{1-8}$alkyl-$R^{10}$, —$C_{2-8}$alkenyl-$R^{10}$, —$C_{2-8}$alkynyl-$R^{10}$, —$C_{1-8}$alkoxy-$R^{10}$, —C(O)H, —C(O)—($C_{1-8}$)alkyl-$R^9$, —C(O)—$NH_2$, —C(O)—NH($C_{1-8}$alkyl-$R^9$), —C(O)—N($C_{1-8}$alkyl-$R^9$)$_2$, —C(O)-cycloalkyl-$R^8$, —C(O)-aryl-$R^8$, —C(NH)—$NH_2$, —$CO_2$H, —C(O)—O—($C_{1-8}$)alkyl-$R^9$, —C(O)—O-aryl-$R^8$, —$SO_2$—($C_{1-8}$) alkyl-$R^9$, —$SO_2$-aryl-$R^8$, —N—$R^7$, cyano, halogen, hydroxy, nitro, -cycloalkyl-$R^8$ and -aryl-$R^6$;

$R^4$ is 1 to 4 substituents attached to a carbon atom independently selected from the group consisting of hydrogen, —$C_{1-8}$alkyl-$R^{10}$, —$C_{2-8}$alkenyl-$R^{10}$, —$C_{2-8}$alkynyl-$R^{10}$, —$C_{1-8}$alkoxy-$R^{10}$, —C(O)H, —C(O)—($C_{1-8}$)alkyl-$R^9$, —C(O)—$NH_2$, —C(O)—NH($C_{1-8}$alkyl-$R^9$), —C(O)—N($C_{1-8}$alkyl-$R^9$)$_2$, —C(O)-cycloalkyl-$R^8$, —C(O)-aryl-$R^8$, —C(NH)—$NH_2$, —$CO_2$H, —C(O)—O—($C_{1-8}$)alkyl-$R^9$, —C(O)—O-aryl-$R^8$, —SH, —S—($C_{1-8}$)alkyl-$R^{10}$, —$SO_2$—($C_{1-8}$)alkyl-$R^9$, —$SO_2$-aryl-$R^8$, —$SO_2$—$NH_2$, —$SO_2$—NH($C_{1-8}$alkyl-$R^9$), —$SO_2$—N($C_{1-8}$alkyl-$R^9$)$_2$, —N—$R^7$, cyano, halogen, hydroxy, nitro, -cycloalkyl-$R^8$, and -aryl-$R^6$;

$R^{10}$ is 1 to 2 substituents independently selected from the group consisting of hydrogen, —$NH_2$, —NH($C_{1-8}$alkyl), —N($C_{1-8}$alkyl)$_2$, cyano, (halo)$_{1-3}$, hydroxy, nitro and oxo; and, Y and Z are independently selected from the group consisting of O, S, (H,OH) and (H,H); with the proviso that one of Y and Z is O and the other is selected from the group consisting of O, S, (H,OH) and (H,H);

or a pharmaceutically acceptable salt thereof.

2. The compound of claim 1 wherein R is selected from the group consisting of $R_a$, —$C_{1-4}$alkyl-$R_a$, —$C_{2-4}$alkenyl-$R_a$, —$C_{2-4}$alkynyl-$R_a$ and cyano.

3. The compound of claim 1 wherein $R^1$ is selected from the group consisting of hydrogen, —$C_{1-4}$alkyl-$R^5$, —$C_{2-4}$alkenyl-$R^5$, —$C_{2-4}$alkynyl-$R^5$, —C(O)—($C_{1-4}$)alkyl-$R^9$, —C(O)-aryl-$R^8$, —C(O)—O—($C_{1-4}$)alkyl-$R^9$, —C(O)—O-aryl-$R^8$, —C(O)—NH($C_{1-4}$alkyl-$R^9$), —C(O)—NH(aryl-$R^8$), —C(O)—N($C_{1-4}$alkyl-$R^9$)$_2$, —$SO_2$—($C_{1-4}$)alkyl-$R^9$, —$SO_2$-aryl-$R^8$, -cycloalkyl-$R^6$, -aryl-$R^6$.

4. The compound of claim 1 wherein $R^1$ is selected from the group consisting of hydrogen, —$C_{1-4}$alkyl-$R^5$ and -aryl-$R^6$.

5. The compound of claim 1 wherein $R^1$ is selected from the group consisting of hydrogen, —$C_{1-4}$alkyl-$R^5$ and -naphthyl-$R^6$.

6. The compound of claim 1 wherein $R^5$ is 1 to 2 substituents independently selected from the group consisting of hydrogen, —O—($C_{1-4}$)alkyl, —O—($C_{1-4}$)alkyl-OH, —O—($C_{1-4}$)alkyl-O—($C_{1-4}$)alkyl, —O—($C_{1-4}$)alkyl-$NH_2$, —O—($C_{1-4}$)alkyl-NH($C_{1-4}$alkyl), —O—($C_{1-4}$)alkyl-N($C_{1-4}$ alkyl)$_2$, —O—($C_{1-4}$)alkyl-S—($C_{1-4}$)alkyl, —O—($C_{1-4}$)alkyl-$SO_2$—($C_{1-4}$)alkyl, —O—($C_{1-4}$)alkyl-$SO_2$—$NH_2$, —O—($C_{1-4}$)alkyl-$SO_2$—NH($C_{1-4}$alkyl), —O—($C_{1-4}$)alkyl-$SO_2$—N($C_{1-4}$alkyl)$_2$, —O—C(O)H, —O—C(O)—($C_{1-4}$)alkyl, —O—C(O)—$NH_2$, —O—C(O)—NH($C_{1-4}$alkyl), —O—C(O)—N($C_{1-4}$alkyl)$_2$, —O—($C_{1-4}$)alkyl-C(O)H, —O—($C_{1-4}$)alkyl-C(O)—($C_{1-4}$)alkyl, —O—($C_{1-4}$)alkyl-$CO_2$H, —O—($C_{1-4}$)alkyl-C(O)—O—($C_{1-4}$)alkyl, —O—($C_{1-4}$)alkyl-C(O)—$NH_2$, —O—($C_{1-4}$)alkyl-C(O)—NH($C_{1-4}$ alkyl), —O—($C_{1-4}$)alkyl-C(O)—N($C_{1-4}$alkyl)$_2$, —C(O)H, —C(O)—($C_{1-4}$)alkyl, —$CO_2$H, —C(O)—O—($C_{1-4}$)alkyl, —C(O)—$NH_2$, —C(NH)—$NH_2$, —C(O)—NH($C_{1-4}$alkyl), —C(O)—N($C_{1-4}$alkyl)$_2$, —SH, —S—($C_{1-4}$)alkyl, —S—($C_{1-4}$)alkyl-S—($C_{1-4}$)alkyl, —S—($C_{1-4}$)alkyl-O—($C_{1-4}$)alkyl, —S—($C_{1-4}$)alkyl-O—($C_{1-4}$)alkyl-OH, —S—($C_{1-4}$)alkyl-O—($C_{1-4}$)alkyl-$NH_2$, —S—($C_{1-4}$)alkyl-O—($C_{1-4}$)alkyl-NH($C_{1-4}$alkyl), —S—($C_{1-4}$)alkyl-O—($C_{1-4}$)alkyl-N($C_{1-4}$alkyl)$_2$, —S—($C_{1-4}$)alkyl-NH($C_{1-4}$alkyl), —$SO_2$—($C_{1-4}$) alkyl, —$SO_2$—$NH_2$, —$SO_2$—NH($C_{1-4}$alkyl), —SO$_2$—N(C$_{1-4}$alkyl)$_2$, —N—R$^7$, cyano, (halo)$_{1-3}$, hydroxy, nitro, oxo, -cycloalkyl-R$^6$, and -aryl-R$^6$.

7. The compound of claim 1 wherein R$^5$ is 1 to 2 substituents independently selected from the group consisting of hydrogen, —O—(C$_{1-4}$)alkyl, —N—R$^7$ and hydroxy.

8. The compound of claim 1 wherein R$^5$ is 1 to 2 substituents independently selected from the group consisting of hydrogen, —O—(C$_{1-4}$)alkyl, —N—R$^7$ and hydroxy.

9. The compound of claim 1 wherein R$^6$ is 1 to 4 substituents attached to a carbon or nitrogen atom independently selected from the group consisting of hydrogen, —C$_{1-4}$alkyl, —C$_{2-4}$alkenyl, —C$_{2-4}$alkynyl, —C(O)H, —C(O)—(C$_{1-4}$)alkyl, —CO$_2$H, —C(O)—O—(C$_{1-4}$)alkyl, —C(O)—NH$_2$, —C(NH)—NH$_2$, —C(O)—NH(C$_{1-4}$alkyl), —C(O)—N(C$_{1-4}$) alkyl)$_2$, —SO$_2$—(C$_{1-4}$)alkyl, —SO$_2$—NH$_2$, —SO$_2$—NH(C$_{1-4}$alkyl), —SO$_2$—N(C$_{1-4}$alkyl)$_2$, —(C$_{1-4}$)alkyl-N—R$^7$, —(C$_{1-4}$)alkyl-(halo)$_{1-3}$, —(C$_{1-4}$)alkyl-OH, -aryl-R$^8$ and —(C$_{1-4}$)alkyl-aryl-R$^8$;
with the proviso that, when R$^6$ is attached to a carbon atom, R$^6$ is further selected from the group consisting of —C$_{1-4}$alkoxy, —(C$_{1-4}$)alkoxy-(halo)$_{1-3}$, —SH, —S—(C$_{1-4}$)alkyl, —N—R$^7$, cyano, halo, hydroxy, nitro and oxo.

10. The compound of claim 1 wherein R$^7$ is 2 substituents independently selected from the group consisting of hydrogen, —C$_{1-4}$alkyl, —C$_{2-4}$alkenyl, —C$_{2-4}$alkynyl, —(C$_{1-4}$)alkyl-OH, —(C$_{1-4}$)alkyl-O—(C$_{1-4}$)alkyl, —(C$_{1-4}$)alkyl-NH$_2$, —(C$_{1-4}$)alkyl-NH(C$_{1-4}$alkyl), —(C$_{1-4}$)alkyl-N(C$_{1-4}$alkyl)$_2$, —(C$_{1-4}$)alkyl-S—(C$_{1-4}$)alkyl, —C(O)H, —C(O)—(C$_{1-4}$)alkyl, —C(O)—O—(C$_{1-4}$)alkyl, —C(O)—NH$_2$, —C(O)—NH(C$_{1-4}$alkyl), —C(O)—N(C$_{1-4}$alkyl)$_2$, —SO$_2$—(C$_{1-4}$)alkyl, —SO$_2$—NH$_2$, —SO$_2$—NH(C$_{1-4}$alkyl), —SO$_2$—N(C$_{1-4}$alkyl)$_2$, —C(N)—NH$_2$, -cycloalkyl-R$^8$, -aryl-R$^8$ and —(C$_{1-4}$)alkyl-aryl-R$^8$.

11. The compound of claim 1 wherein R$^7$ is 2 substituents independently selected from the group consisting of hydrogen, —C$_{1-4}$alkyl, —C(O)H, —C(O)—(C$_{1-4}$)alkyl, —C(O)—O—(C$_{1-4}$)alkyl, —SO$_2$—NH$_2$, —SO$_2$—NH(C$_{1-4}$alkyl) and —SO$_2$—N(C$_{1-4}$alkyl)$_2$.

12. The compound of claim 1 wherein R$^8$ is 1 to 4 substituents attached to a carbon or nitrogen atom independently selected from the group consisting of hydrogen, —C$_{1-4}$alkyl, —(C$_{1-4}$)alkyl-(halo)$_{1-3}$ and —(C$_{1-4}$)alkyl-OH;
with the proviso that, when R$^8$ is attached to a carbon atom, R$^8$ is further selected from the group consisting of —C$_{1-4}$alkoxy, —NH$_2$, —NH(C$_{1-4}$alkyl), —N(C$_{1-4}$alkyl)$_2$, cyano, halo, —(C$_{1-4}$)alkoxy-(halo)$_{1-3}$, hydroxy and nitro.

13. The compound of claim 1 wherein R$^9$ is 1 to 2 substituents independently selected from the group consisting of hydrogen, —C$_{1-4}$alkoxy, —NH$_2$, —NH(C$_{1-4}$alkyl), —N(C$_{1-4}$ alkyl)$_2$, cyano, (halo)$_{1-3}$, hydroxy and nitro.

14. The compound of claim 1 wherein R$^6$, R$^8$ and R$^9$ are hydrogen.

15. The compound of claim 1 wherein R$^2$ is one substituent attached to a carbon or nitrogen atom selected from the group consisting of hydrogen, —C$_{1-4}$alkyl-R$^5$, —C$_{2-4}$alkenyl-R$^5$, —C$_{2-4}$alkynyl-R$^5$, —C(O)H, —C(O)—(C$_{1-4}$)alkyl-R$^9$, —C(O)—NH$_2$, —C(O)—NH(C$_{1-4}$alkyl-R$^9$), —C(O)—N(C$_{1-4}$alkyl-R$^9$)$_2$, —C(O)—NH(aryl-R$^8$), —C(O)-cycloalkyl-R$^8$, —C(O)-aryl-R$^8$, —CO$_2$H, —C(O)—O—(C$_{1-4}$)alkyl-R$^9$, —C(O)—O-aryl-R$^8$, —SO$_2$—(C$_{1-4}$)alkyl-R$^9$, —SO$_2$-aryl-R$^8$, -cycloalkyl-R$^6$, -aryl-R$^6$ and —(C$_{1-4}$)alkyl-N—R$^7$;
with the proviso that, when R$^2$ is attached to a carbon atom, R$^2$ is further selected from the group consisting of —C$_{1-4}$alkoxy-R$^5$, —N—R$^7$, cyano, halogen, hydroxy, nitro and oxo.

16. The compound of claim 1 wherein R$^2$ is one substituent attached to a carbon or nitrogen atom selected from the group consisting of hydrogen, —C$_{1-4}$alkyl-R$^5$, —C$_{2-4}$alkenyl-R$^5$, —C$_{2-4}$alkynyl-R$^5$, —CO$_2$H, —C(O)—O—(C$_{1-4}$)alkyl-R$^9$, -cycloalkyl-R$^6$, -aryl-R$^6$ and —(C$_{1-4}$)alkyl-N—R$^7$;
with the proviso that, when R$^2$ is attached to a nitrogen atom, a quaternium salt is not formed; and, with the proviso that, when R$^2$ is attached to a carbon atom, R$^2$ is further selected from the group consisting of —C$_{1-4}$alkoxy-R$^5$, —N—R$^7$, cyano, halogen, hydroxy, nitro and oxo.

17. The compound of claim 1 wherein R$^2$ is one substituent attached to a carbon or nitrogen atom selected from the group consisting of hydrogen, —C$_{1-4}$alkyl-R$^5$ and -aryl-R$^6$; with the proviso that when R$^2$ is attached to a nitrogen atom, a quaternium salt is not formed; and, with the proviso that when R$^2$ is attached to a carbon atom, R$^2$ is further selected from the group consisting of —N—R$^7$, halogen and hydroxy.

18. The compound of claim 1 wherein R$^3$ is 1 to 3 substituents attached to a carbon atom independently selected from the group consisting of hydrogen, —C$_{1-4}$alkyl-R$^{10}$, —C$_{2-4}$alkenyl-R$^{10}$, —C$_{2-4}$alkynyl-R$^{10}$, —C$_{1-4}$alkoxy-R$^{10}$, —C(O)H, —C(O)—(C$_{1-4}$)alkyl-R$^9$, —C(O)—NH$_2$, —C(O)—NH(C$_{1-4}$alkyl-R$^9$), —C(O)—N(C$_{1-4}$alkyl-R$^9$)$_2$, —C(O)-cycloalkyl-R$^8$, —C(O)-aryl-R$^8$, —C(NH)—NH$_2$, —CO$_2$H, —C(O)—O—(C$_{1-4}$)alkyl-R$^9$, —C(O)-O-aryl-R$^8$, —SO$_2$—(C$_{1-8}$)alkyl-R$^9$, —SO$_2$-aryl-R$^8$, —N—R$^7$, —(C$_{1-4}$)alkyl-N—R$^7$, cyano, halogen, hydroxy, nitro, -cycloalkyl-R$^8$ and -aryl-R$^8$.

19. The compound of claim 1 wherein R is one substituent attached to a carbon atom selected from the group consisting of hydrogen, —C$_{1-4}$alkyl-R$^{10}$, —C$_{2-4}$alkenyl-R$^{10}$, —C$_{2-4}$alkynyl-R$^{10}$, —C$_{1-4}$alkoxy-R$^{10}$, —C(O)H, —CO$_2$H, —NH$_2$, —NH(C$_{1-4}$alkyl), —N(C$_{1-4}$alkyl)$_2$, cyano, halogen, hydroxy and nitro.

20. The compound of claim 1 wherein R$^3$ is one substituent attached to a carbon atom selected from the group consisting of hydrogen, —C$_{1-4}$alkyl-R$^{10}$, —NH$_2$, —NH(C$_{1-4}$alkyl), —N(C$_{1-4}$alkyl)$_2$, halogen and hydroxy.

21. The compound of claim 1 wherein R$^4$ is 1 to 4 substituents attached to a carbon atom independently selected from the group consisting of hydrogen, —C$_{1-4}$alkyl-R$^{10}$, —C$_{2-4}$alkenyl-R$^{10}$, —C$_{2-4}$alkynyl-R$^{10}$, —C$_{1-4}$alkoxy-R$^{10}$, —C(O)H, —C(O)—(C$_{1-4}$)alkyl-R$^9$, —C(O)—NH$_2$, —C(O)—NH(C$_{1-4}$alkyl-R$^9$), —C(O)—N(C$_{1-4}$alkyl-R$^9$)$_2$, —C(O)-cycloalkyl-R$^8$, —C(O)-aryl-R$^8$, —C(NH)—NH$_2$, —CO$_2$H, —C(O)—O—(C$_{1-4}$)alkyl-R$^9$, —C(O)—O-aryl-R$^8$, —SH, —S—(C$_{1-4}$)alkyl-R$^{10}$, —SO$_2$—(C$_{1-4}$)alkyl-R$^9$, —SO$_2$-aryl-R$^8$, —SO$_2$—NH$_2$, —SO$_2$—NH(C$_{1-4}$alkyl-R$^9$), —SO$_2$—N(C$_{1-4}$alkyl-R$^9$)$_2$, —N—R$^7$, cyano, halogen, hydroxy, nitro, -cycloalkyl-R$^8$ and -aryl-R$^8$.

22. The compound of claim 1 wherein R$^4$ is 1 to 4 substituents attached to a carbon atom independently selected from the group consisting of hydrogen, —C$_{1-4}$alkyl-R$^{10}$, —C$_{2-4}$alkenyl-R$^{10}$, —C$_{2-4}$alkynyl-R$^{10}$, —C$_{1-4}$alkoxy-R$^{10}$, —C(O)H, —CO$_2$H, —NH$_2$, —NH(C$_{1-4}$alkyl), —N(C$_{1-4}$alkyl)$_2$, cyano, halogen, hydroxy, nitro and -cycloalkyl, -aryl.

23. The compound of claim 1 wherein R$^4$ is 1 to 4 substituents attached to a carbon atom independently selected from the group consisting of hydrogen, C$_{1-4}$alkyl-R$^{10}$, C$_{1-4}$alkoxy-R$^{10}$, —NH$_2$, —NH(C$_{1-4}$alkyl), —N(C$_{1-4}$alkyl)$_2$, halogen and hydroxy.

24. The compound of claim 1 wherein R$^4$ is 1 to 4 substituents attached to a carbon atom independently selected from the group consisting of hydrogen, C$_{1-4}$alkyl-R$^{10}$, C$_{1-4}$alkoxy-R$^{10}$, —NH$_2$, —NH(C$_{1-4}$alkyl), —N(C$_{1-4}$alkyl)$_2$, chlorine, fluorine and hydroxy.

25. The compound of claim 1 wherein $R^{10}$ is 1 to 2 substituents independently selected from the group consisting of hydrogen, —$NH_2$, —$NH(C_{1-4}alkyl)$, —$N(C_{1-4}alkyl)_2$, cyano, $(halo)_{1-3}$, hydroxy, nitro and oxo.

26. The compound of claim 1 wherein $R^{10}$ is 1 to 2 substituents independently selected from the group consisting of hydrogen and $(halo)_{1-3}$.

27. The compound of claim 1 wherein $R^{10}$ is 1 to 2 substituents independently selected from the group consisting of hydrogen and $(fluoro)_3$.

28. The compound of claim 1 wherein Y and Z are independently selected from the group consisting of O, S, (H,OH) and (H,H); with the proviso that one of Y and Z is O and the other is selected from the group consisting of O, S, (H,OH) and (H,H).

29. The compound of claim 1 wherein Y and Z are independently selected from the group consisting of O and (H,H); with the proviso that one of Y and Z is O, and the other is selected from the group consisting of O and (H,H).

30. The compound of claim 1 wherein Y and Z are independently selected from O.

31. The compound of claim 1 wherein the compound of Formula (I) is a compound selected from Formula (Ia):

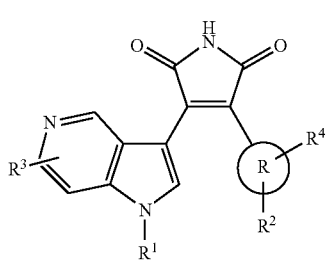

Formula (Ia)

wherein R, $R^1$, $R^2$, $R^3$ and $R^4$ are dependently selected from:

| $R^1$ | $R^3$ | R | $R^2$ | $R^4$ |
|---|---|---|---|---|
| $CH_3O(CH_2)_3$ | H | Ph | H | 2-OMe; |
| $CH_3O(CH_2)_3$ | H | Ph | H | 2-Cl. |

\* \* \* \* \*